US012605465B2

(12) United States Patent (10) Patent No.: US 12,605,465 B2

Fu et al. (45) Date of Patent: Apr. 21, 2026

(54) AAV-NAGLU VECTORS FOR TREATMENT OF MUCOPOLYSACCHARIDOSIS IIIB

(71) Applicant: The University of North Carolina at Chapel Hill, Chapel Hill, NC (US)

(72) Inventors: Haiyan Fu, Durham, NC (US); Tierra Bobo, Mebane, NC (US)

(73) Assignee: The University of North Carolina at Chapel Hill, Chapel Hill, NC (US)

( * ) Notice: Subject to any disclaimer, the term of this patent is extended or adjusted under 35 U.S.C. 154(b) by 692 days.

(21) Appl. No.: 17/907,025

(22) PCT Filed: Mar. 22, 2021

(86) PCT No.: PCT/US2021/023383

§ 371 (c)(1),
(2) Date: Sep. 22, 2022

(87) PCT Pub. No.: WO2021/194915

PCT Pub. Date: Sep. 30, 2021

(65) Prior Publication Data

US 2023/0149564 A1 May 18, 2023

Related U.S. Application Data

(60) Provisional application No. 62/993,266, filed on Mar. 23, 2020.

(51) Int. Cl.
A61K 48/00 (2006.01)
C12N 9/24 (2006.01)
C12N 15/86 (2006.01)

(52) U.S. Cl.
CPC .......... A61K 48/005 (2013.01); C12N 9/2402 (2013.01); C12N 15/86 (2013.01); *C12Y 302/0105* (2013.01)

(58) Field of Classification Search
CPC .... A61K 48/005; C12N 9/2402; C12N 15/86; C12Y 302/0105
See application file for complete search history.

(56) References Cited

U.S. PATENT DOCUMENTS

| | | | |
|---|---|---|---|
| 9,220,755 B2 * | 12/2015 | Chakraborty | .......... A61K 47/54 |
| 10,538,589 B2 | 1/2020 | Pardridge et al. | |
| 2017/0216412 A1 | 8/2017 | Quinn et al. | |
| 2020/0000887 A1 | 1/2020 | McCarty et al. | |

FOREIGN PATENT DOCUMENTS

| | | |
|---|---|---|
| WO | 2009131698 A2 | 10/2009 |
| WO | 2019108856 A1 | 6/2019 |

OTHER PUBLICATIONS

Meadows et al. (Mol Ther Methods Clin Dev. Apr. 19, 2019:13:453-462. doi: 10.1016/j.omtm.2019.04.004. eCollection Jun. 14, 2019) (Year: 2019).*
Holley et al. (Brain. Jan. 1, 2018;141(1):99-116. doi: 10.1093/brain/awx311.) (Year: 2018).*
"International Search Report and Written Opinion corresponding International Application No. PCT/US2021/023383 mailed Jul. 6, 2021".
Cressant, Arnaud , et al., "Improved Behavior and Neuropathology in the Mouse Model of Sanfilippo Type IIIB Disease after Adeno-Associated Virus-Mediated Gene Transfer in the Striatum", The Journal of Neuroscience 24(45):10229-10239 (Nov. 10, 2004).
"International Preliminary Report on Patentability corresponding International Application No. PCT/US2021/023383 mailed Oct. 6, 2022".
"Extended European Search Report corresponding to European Application No. EP21775145.2 dated Feb. 27, 2024".

* cited by examiner

*Primary Examiner* — Fereydoun G Sajjadi
*Assistant Examiner* — Joel D Levin
(74) *Attorney, Agent, or Firm* — Myers Bigel, P.A.

(57) ABSTRACT

Recombinant nucleic acid comprising nucleotides encoding α-N-acetylglucosaminidase (NAGLU). Vectors comprising the recombinant nucleic acid for delivery to a subject. In an aspect the NAGLU sequences optimized for expression in human cells. Methods of using the vector to increase secretion of NAGLU from a cell and for treatment and prevention of mucopolysaccharidosis IIIB.

19 Claims, 10 Drawing Sheets

Specification includes a Sequence Listing.

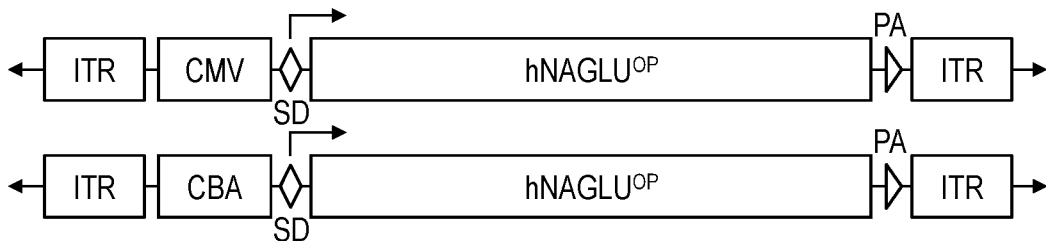
*FIG. 1*
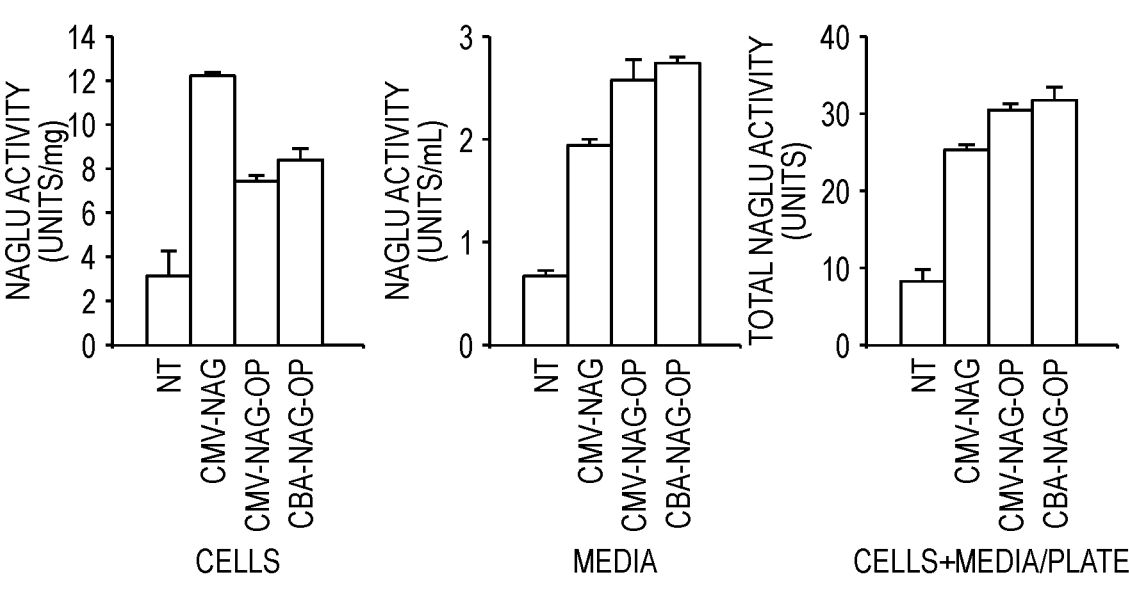
*FIG. 2A*        *FIG. 2B*        *FIG. 2C*

SEQUENCE LISTING

```
<160> NUMBER OF SEQ ID NOS: 4

<210> SEQ ID NO 1
<211> LENGTH: 2232
<212> TYPE: DNA
<213> ORGANISM: Artificial
<220> FEATURE:
<223> OTHER INFORMATION: codon-optimized alpha-N-acetylglucosaminidase

<400> SEQUENCE: 1
atggaggctg ttgctgttgc agccgctgtg ggcgtcttgc tgttggccgg tgccggggga      60
gctgctggcg acgaggcaag ggaagctgca gctgtgcggg ctctcgtcgc aaggttgctg     120
ggtccaggtc ccgctgctga ctttagtgtg tcagtggaga gggctttggc cgctaaacct     180
ggcctggaca cctactccct gggtggaggt ggggctgccc gcgtgagggt gagaggctca     240
acgggggtgg ctgctgcagc aggtctgcat aggtacctca gagacttctg cggatgccat     300
gtcgcttgga gcggcagtca actgaggctg cccgggcccc tccctgccgt ccctggggaa     360
cttacagaag ctactccaaa taggtacaga tattatcaaa atgtgtgtac gcagagttac     420
agctttgtgt ggtgggactg ggcaaggtgg gagcgcgaaa tcgattggat ggccctcaac     480
gggatcaatc tggccttggc atggtccgga caggaagcta tctggcagcg cgtgtatctg     540
gctctcgggt tgactcaagc tgaaatcaac gagtttttca caggccccgc cttcctggcc     600 tggggcgga tgggtaatct tcatacttgg gacgggccac tgcccccctc ttggcacatc     660
aaacagttgt atctgcagca ccgcgtcctg gaccagatgc gcagcttcgg catgactccc     720
gtcctgccgg ctttcgcagg gcacgtccca gaggcggtca cacgggtctt ccctcaggtg     780
aatgtgacaa aaatgggatc atggggacat ttcaattgtt cttacagttg ttccttcctg     840
ctggcacccg aagatcctat cttcccaatc ataggaagtc tctttctgcg cgagttgatt     900
aaggagttcg gtactgatca catttatggc gctgatactt ttaacgaaat gcagccccc     960 tcttctgaac catcctatct tgctgccgca accactgccg tttatgaagc catgaccgcc    1020
gtggacactg aagccgtttg gcttctccaa ggttggctgt tccagcacca gcctcagttt    1080 tggggccag ctcagataag agccgttctc ggcgctgtac ctcgcggaag actgctggtg    1140
cttgatttgt tcgcagagtc tcagccagtg tacacgagaa ccgcttcctt ccagggccag    1200
```

-continued

```
ccgtttattt ggtgtatgct tcacaatttt ggcggaaatc atgggctgtt cggtgccctg      1260
gaggccgtca atgggggacc tgaggctgca agattgttcc caaactcaac catggtgggg      1320
accggaatgg cacccgaagg cattagccag aatgaggtcg tctacagtct gatggcggaa      1380
ttggggtggc ggaaggaccc cgtgccagat ctcgccgcct gggtgactag ctttgccgcc      1440
cgccgctatg gagtgagcca tcctgatgca ggcgcagcct ggcggctgtt gcttcgatca      1500
gtatacaatt gttcaggaga ggcctgccgg gggcacaata ggagcccact ggtaaggagg      1560
cccagcctgc agatgaacac ctctatctgg tacaacagaa gcgatgtttt cgaggcttgg      1620
agacttctcc ttacatctgc ccctagcttg gccaccagtc cagccttccg atatgatctg      1680
ctggacctca cccgacaggc cgtgcaggaa ctggtctctc tctactatga agaggccaga      1740
tcagcttacc tctctaaaga actggcctcc ctcttgcgag caggaggcgt cctggcatat      1800
gagctgctcc ctgcactgga cgaggtactg gcatctgatt cccgattcct gctcgggtca      1860
tggctggagc aagcccgagc agcggctgta agcgaggctg aagcagactt ctatgaacaa      1920
aatagtaggt atcaactgac tctgtggggt ccagagggga atatcctgga ctacgcgaac      1980
aaacagttgg cgggcctggt ggccaactac tacacccctc ggtggagatt gtttttggag      2040
gcgctggtgg attcagtcgc acaggggatt ccgtttcagc aacatcagtt tgacaagaac      2100
gtctttcagc tggaacaggc ttttgtgctt tctaagcagc gctacccttc tcagccaaga      2160
ggcgataccg ttgacctcgc gaagaaaatc tttctcaagt actatcccag atgggtggcc      2220
ggatcatggt ag                                                         2232

<210> SEQ ID NO 2
<211> LENGTH: 2232
<212> TYPE: DNA
<213> ORGANISM: Homo sapiens

<400> SEQUENCE: 2
atggaggcgg tggcggtggc cgcggcggtg ggggtccttc tcctggccgg ggccgggggc        60
gcggcaggcg acgaggcccg ggaggcggcg gccgtgcggg cgctcgtggc ccggctgctg       120
gggccaggcc ccgcggccga cttctccgtg tcggtggagc gcgctctggc tgccaagccg       180
ggcttggaca cctacagcct ggggcggcgg ggcgcggcgc gcgtgcgggt gcgcggctcc       240
acgggcgtgg cggccgccgc ggggctgcac cgctacctgc gcgacttctg tggctgccac       300
gtggcctggt ccggctctca gctgcgcctg ccgcggccac tgccagccgt gccggggggag       360 ctgaccgagg ccacgcccaa caggtaccgc tattaccaga atgtgtgcac gcaaagctac       420
tccttcgtgt ggtgggactg ggcccgctgg gagcgagaga tagactggat ggcgctgaat       480
ggcatcaacc tggcactggc ctggagcggc caggaggcca tctggcagcg ggtgtacctg       540
gccttgggcc tgacccaggc agagatcaat gagttcttta ctggtcctgc cttcctggcc       600
tgggggcgaa tgggcaacct gcacacctgg gatggccccc tgcccccctc ctggcacatc       660
aagcagcttt acctgcagca ccgggtcctg gaccagatgc gctccttcgg catgaccccca       720 gtgctgcctg cattcgcggg gcatgttccc gaggctgtca ccagggtgtt ccctcaggtc       780
aatgtcacga agatgggcag ttggggccac tttaactgtt cctactcctg ctccttcctt       840
ctggctccgg aagaccccat attccccatc atcgggagcc tcttcctgcg agagctgatc       900
aaagagtttg gcacagacca catctatggg gccgacactt tcaatgagat gcagccacct       960
tcctcagagc cctcctacct tgccgcagcc accactgccg tctatgaggc catgactgca      1020
```

-continued

```
gtggatactg aggctgtgtg gctgctccaa ggctggctct tccagcacca gccgcagttc      1080
tgggggcccg cccagatcag ggctgtgctg ggagctgtgc cccgtggccg cctcctggtt      1140
ctggacctgt ttgctgagag ccagcctgtg tatacccgca ctgcctcctt ccagggccag      1200
cccttcatct ggtgcatgct gcacaacttt gggggaaacc atggtctttt tggagcccta      1260
gaggctgtga acggaggccc agaagctgcc cgcctcttcc ccaactccac catggtaggc      1320
acgggcatgg cccccgaggg catcagccag aacgaagtgg tctattccct catggctgag      1380
ctgggctggc gaaaggaccc agtgccagat ttggcagcct gggtgaccag ctttgccgcc      1440
cggcggtatg gggtctccca cccggacgca ggggcagcgt ggaggctact gctccggagt      1500
gtgtacaact gctccgggga ggcctgcagg ggccacaatc gtagcccgct ggtcaggcgg      1560
ccgtccctac agatgaatac cagcatctgg tacaaccgat ctgatgtgtt tgaggcctgg      1620
cggctgctgc tcacatctgc tccctccctg gccaccagcc ccgccttccg ctacgacctg      1680
ctggacctca ctcggcaggc agtgcaggag ctggtcagct tgtactatga ggaggcaaga      1740
agcgcctacc tgagcaagga gctggcctcc ctgttgaggg ctggaggcgt cctggcctat      1800
gagctgctgc cggcactgga cgaggtgctg gctagtgaca gccgcttctt gctgggcagc      1860
tggctagagc aggcccgagc agcggcagtc agtgaggccg aggccgattt ctacgagcag      1920
aacagccgct accagctgac cttgtggggg ccagaaggca acatcctgga ctatgccaac      1980
aagcagctgg cggggttggt ggccaactac tacacccctc gctggcggct tttcctggag      2040
gcgctggttg acagtgtggc ccagggcatc cctttccaac agcaccagtt tgacaaaaat      2100
gtcttccaac tggagcaggc cttcgttctc agcaagcaga ggtaccccag ccagccgcga      2160
ggagacactg tggacctggc caagaagatc ttcctcaaat attaccccgg ctgggtggcc      2220
ggctcttggt ga                                                          2232
```

<210> SEQ ID NO 3
<211> LENGTH: 7730
<212> TYPE: DNA
<213> ORGANISM: Artificial
<220> FEATURE:
<223> OTHER INFORMATION: plasmid

<400> SEQUENCE: 3

```
ggggggggg ggggggggtt ggccactccc tctctgcgcg ctcgctcgct cactgaggcc       60
gggcgaccaa aggtcgcccg acgcccgggc tttgcccggg cggcctcagt gagcgagcga      120
gcgcgcagag agggagtggc caactccatc actaggggtt cctagatctg gaagctgatc      180
ttcaatattg gccattagcc atattattca ttggttatat agcataaatc aatattggat      240
attggccatt gcatacgttg tatctatatc ataatatgta catttatatt ggctcatgtc      300
caatatgacc gccatgttgg cattgattat tgactagtta ttaatagtaa tcaattacgg      360
ggtcattagt tcatagccca tatatggagt tccgcgttac ataacttacg gtaaatggcc      420
cgcctggctg accgcccaac gacccccgcc cattgacgtc aataatgacg tatgttccca      480
tagtaacgcc aatagggact ttccattgac gtcaatgggt ggagtattta cggtaaactg      540
cccacttggc agtacatcaa gtgtatcata tgccaagtcc gcccctatt gacgtcaatg       600 acggtaaatg gcccgcctgg cattatgccc agtacatgac cttacgggac tttcctactt      660
ggcagtacat ctacgtatta gtcatcgcta ttaccatggt cgaggtgagc cccacgttct      720
gcttcactct ccccatctcc cccccctccc cacccccaat tttgtattta tttatttttt      780
aattattttg tgcagcgatg ggggcggggg ggggggggg gcgcgcgcca ggcggggcgg       840
```

-continued

```
ggcggggcga ggggcggggc ggggcgaggc ggagaggtgc ggcggcagcc aatcagagcg      900
gcgcgctccg aaagtttcct tttatggcga ggcggcggcg cgcggcggcc tataaaaagc      960
gaagcgcgcg cgcgggcggga gtcgctgcga cgctgccttc gccccgtgcc ccgctccgcc     1020
gccgcctcgc gccgcccgcc ccggctctga ctgaccgcgt tactcccaca ggtgagcggg     1080
cgggacggcc cttctcctcc gggctgtaat tagcgcttgg tttaatgacg gcttgtttct     1140
tttctgtggc tgcgtgaaag ccttgagggg ctccgggagg gccctttgtg cggggggggag     1200 cggctcgggg ggtgcgtgcg tgtgtgtgtg cgtggggagc gccgcgtgcg gcccgcgctg     1260 cccgcggct gtgagcgctg cgggcgcggc gcggggcttt gtgcgctccg cagtgtgcgc      1320
gaggggagcg cggccggggg cggtgccccg cggtgcgggg ggggctgcga ggggaacaaa     1380
ggctgcgtgc ggggtgtgtg cgtgggggggg tgagcagggg gtatgggcgc ggcggtcggg     1440
ctgtaacccc cccctgcacc cccctccccg agttgctgag cacggcccgg cttcgggtgc     1500
ggggctccgt acggggcgtg gcgcggggct cgccgtgccg ggcgggggggt ggcggcaggt     1560 gggggtgccg ggcggggcgg ggccgcctcg ggccggggag ggctcggggg aggggcgcgg     1620
cggcccccgg agcgccggcg gctgtcgagg cgcggcgagc cgcagccatt gccttttatg     1680
gtaatcgtgc gagagggcgc agggacttac tttgtcccaa atctgtgcgg agccgaaatc     1740
tgggaggcgc cgccgcaccc cctctagcgg gcgcggggcg aagcggtgcg cgcgccggcag     1800 gaaggaaatg ggcggggagg gccttcgtgc gtcgccgcgc cgccgtcccc ttctccctct     1860
ccagcctcgg ggctgtccgc ggggggacgg ctgccttcgg gggggacggg gcagggcggg     1920
gttcggcttc tggcgtgtga ccggcggctc tagagcctct gctaaccatg ttcatgcctt     1980
cttctttttc ctacagctcc tgggcaacgt gctggttatt gtgctgtctc atcattttgg     2040
caaagaattc gataggatcc ggtactcgag gaactgaaaa accagaaagt taactggtaa     2100
gtttagtctt tttgtctttt atttcaggtc ccggatccgg tggtggtgca aatcaaagaa     2160
ctgctcctca gtggatgttg cctttacttc taggcctgta cggaagtgtt acttctgctc     2220
taaaagctgc ggaattgtac ccgcggcccg ggatccaccg gccaccggta ttcgcagacc     2280
atggaggctg ttgctgttgc agccgctgtg ggcgtcttgc tgttggccgg tgccggggga     2340
gctgctggcg acgaggcaag ggaagctgca gctgtgcggg ctctcgtcgc aaggttgctg     2400
ggtccaggtc ccgctgctga ctttagtgtg tcagtggaga gggctttggc cgctaaacct     2460
ggcctggaca cctactccct gggtggaggt ggggctgccc gcgtgagggt gagaggctca     2520
acgggggtgg ctgctgcagc aggtctgcat aggtacctca gagacttctg cggatgccat     2580
gtcgcttgga gcggcagtca actgaggctg ccccggcccc tccctgccgt ccctggggaa     2640
cttacagaag ctactccaaa taggtacaga tattatcaaa atgtgtgtac gcagagttac     2700
agctttgtgt ggtgggactg ggcaaggtgg gagcgcgaaa tcgattggat ggccctcaac     2760
gggatcaatc tggccttggc atggtccgga caggaagcta tctggcagcg cgtgtatctg     2820
gctctcgggt tgactcaagc tgaaatcaac gagtttttca caggccccgc cttcctggcc     2880 tggggggcgga tgggtaatct tcatacttgg gacgggccac tgcccccctc ttggcacatc     2940
aaacagttgt atctgcagca ccgcgtcctg gaccagatgc gcagcttcgg catgactccc     3000
gtcctgccgg ctttcgcagg gcacgtccca gaggcggtca cacgggtctt ccctcaggtg     3060
aatgtgacaa aaatgggatc atggggacat ttcaattgtt cttacagttg ttccttcctg     3120
ctggcacccg aagatcctat cttcccaatc ataggaagtc tctttctgcg cgagttgatt     3180
```

-continued

```
aaggagttcg gtactgatca catttatggc gctgatactt ttaacgaaat gcagccccc        3240 tcttctgaac catcctatct tgctgccgca accactgccg tttatgaagc catgaccgcc        3300
gtggacactg aagccgtttg gcttctccaa ggttggctgt tccagcacca gcctcagttt        3360 tggggggccag ctcagataag agccgttctc ggcgctgtac ctcgcggaag actgctggtg       3420
cttgatttgt tcgcagagtc tcagccagtg tacacgagaa ccgcttcctt ccagggccag        3480
ccgtttattt ggtgtatgct tcacaatttt ggcggaaatc atgggctgtt cggtgccctg        3540
gaggccgtca atgggggacc tgaggctgca agattgttcc caaactcaac catggtgggg        3600
accggaatgg cacccgaagg cattagccag aatgaggtcg tctacagtct gatggcggaa        3660
ttggggtggc ggaaggaccc cgtgccagat ctcgccgcct gggtgactag ctttgccgcc        3720
cgccgctatg gagtgagcca tcctgatgca ggcgcagcct ggcggctgtt gcttcgatca        3780
gtatacaatt gttcaggaga ggcctgccgg gggcacaata ggagcccact ggtaaggagg        3840
cccagcctgc agatgaacac ctctatctgg tacaacagaa gcgatgtttt cgaggcttgg       3900
agacttctcc ttacatctgc ccctagcttg gccaccagtc cagccttccg atatgatctg       3960
ctggacctca cccgacaggc cgtgcaggaa ctggtctctc tctactatga agaggccaga       4020
tcagcttacc tctctaaaga actggcctcc ctcttgcgag caggaggcgt cctggcatat       4080
gagctgctcc ctgcactgga cgaggtactg gcatctgatt cccgattcct gctcgggtca       4140
tggctggagc aagcccgagc agcggctgta agcgaggctg aagcagactt ctatgaacaa       4200
aatagtaggt atcaactgac tctgtggggt ccagagggga atatcctgga ctacgcgaac       4260
aaacagttgg cgggcctggt ggccaactac tacacccctc ggtggagatt gttttttggag      4320 gcgctggtgg attcagtcgc acaggggatt ccgtttcagc aacatcagtt tgacaagaac       4380
gtctttcagc tggaacaggc ttttgtgctt tctaagcagc gctacccttc tcagccaaga       4440
ggcgataccg ttgacctcgc gaagaaaatc tttctcaagt actatcccag atgggtggcc       4500
ggatcatggt aggtcgaccc tcgactagag ctcgctgatc agcctcgact gtgccttcta       4560
gttgccagcc atctgttgtt tgcccctccc ccgtgccttc cttgaccctg gaaggtgcca       4620
ctcccactgt cctttcctaa taaaatgagg aaattgcatc gcattgtctg agtaggtgtc       4680
attctattct ggggggtggg gtggggcagg acagcaaggg ggaggattgg gaagacaata       4740
gcaggcatgc tggggagaga ctaggaacc cctagtgatg gagttggcca ctccctctct        4800
gcgcgctcgc tcgctcactg aggccgcccg ggcaaagccc gggcgtcggg cgacctttgg       4860
tcgcccggcc tcagtgagcg agcgagcgcg cagagaggga gtggccaacc ccccccccc        4920 cccccctgca gccagctggc gtaatagcga agaggcccgc accgatcgcc cttcccaaca       4980
gttgcgtagc ctgaatggcg aatgcgcgca gcgccctgt agcggcgcat taagcgcggc        5040
gggtgtggtg gttacgcgca gcgtgaccgc tacacttgcc agcgccctag cgcccgctcc       5100
tttcgctttc ttcccttcct ttctcgccac gttcgccggc tttccccgtc aagctctaaa       5160 tcggggggctc cctttagggt tccgatttag tgctttacgg cacctcgacc ccaaaaaact      5220
tgattagggt gatggttcac gtagtgggcc atcgccctga tagacggttt ttcgcccttt       5280
gacgttggag tccacgttct ttaatagtgg actcttgttc caaactggaa caacactcaa       5340
ccctatctcg gtctattctt ttgatttata agggattttg ccgatttcgg cctattggtt       5400
aaaaaatgag ctgatttaac aaaaatttaa cgcgaatttt aacaaaatat taacgtttac       5460
aatttcctga tgcggtattt tctccttacg catctgtgcg gtatttcaca ccgcatatgg       5520
tgcactctca gtacaatctg ctctgatgcc gcatagttaa gccagccccg acacccgcca       5580
```

-continued

```
acacccgctg acgcgccctg acgggcttgt ctgctcccgg catccgctta cagacaagct    5640
gtgaccgtct ccgggagctg catgtgtcag aggtttttcac cgtcatcacc gaaacgcgcg    5700
agacgaaagg gcctcgtgat acgcctattt ttataggtta atgtcatgat aataatggtt    5760
tcttagacgt caggtggcac ttttcgggga aatgtgcgcg gaaccccctat ttgtttattt    5820 ttctaaatac attcaaatat gtatccgctc atgagacaat aaccctgata aatgcttcaa    5880
taatattgaa aaaggaagag tatgagtatt caacatttcc gtgtcgccct tattcccttt    5940
tttgcggcat tttgccttcc tgtttttgct cacccagaaa cgctggtgaa agtaaaagat    6000
gctgaagatc agttgggtgc acgagtgggt tacatcgaac tggatctcaa cagcggtaag    6060
atccttgaga gttttcgccc cgaagaacgt tttccaatga tgagcacttt taaagttctg    6120
ctatgtggcg cggtattatc ccgtattgac gccgggcaag agcaactcgg tcgccgcata    6180
cactattctc agaatgactt ggttgagtac tcaccagtca cagaaaagca tcttacggat    6240
ggcatgacag taagagaatt atgcagtgct gccataacca tgagtgataa cactgcggcc    6300
aacttacttc tgacaacgat cggaggaccg aaggagctaa ccgcttttttt gcacaacatg    6360 gggggatcatg taactcgcct tgatcgttgg gaaccggagc tgaatgaagc cataccaaac    6420
gacgagcgtg acaccacgat gcctgtagca atggcaacaa cgttgcgcaa actattaact    6480
ggcgaactac ttactctagc ttcccggcaa caattaatag actggatgga ggcggataaa    6540
gttgcaggac cacttctgcg ctcggccctt ccggctggct ggtttattgc tgataaatct    6600
ggagccggtg agcgtgggtc tcgcggtatc attgcagcac tggggccaga tggtaagccc    6660
tcccgtatcg tagttatcta cacgacgggg agtcaggcaa ctatgacctt ccagggtcaa    6720
ggaagctgtc agaccaagtt tactcatata tactttagat tgatttaaaa cttcattttt    6780
aatttaaaag gatctaggtg aagatccttt ttgataatct catgaccaaa atcccttaac    6840
gtgagttttc gttccactga gcgtcagacc ccgtagaaaa gatcaaagga tcttcttgag    6900
atcctttttt tctgcgcgta atctgctgct tgcaaacaaa aaaaccaccg ctaccagcgg    6960
tggtttgttt gccggatcaa gagctaccaa ctcttttttcc gaaggtaact ggcttcagca    7020
gagcgcagat accaaatact gtccttctag tgtagccgta gttaggccac cacttcaaga    7080
actctgtagc accgcctaca tacctcgctc tgctaatcct gttaccagtg gctgctgcca    7140
gtggcgataa gtcgtgtctt accgggttgg actcaagacg atagttaccg gataaggcgc    7200
agcggtcggg ctgaacgggg ggttcgtgca cacagcccag cttggagcga acgacctaca    7260
ccgaactgag atacctacag cgtgagcatt gagaaagcgc cacgcttccc gaagggagaa    7320
aggcggacag gtatccggta agcggcaggg tcggaacagg agagcgcacg agggagcttc    7380
cagggggaaa cgcctggtat ctttatagtc ctgtcgggtt tcgccacctc tgacttgagc    7440
gtcgattttt gtgatgctcg tcaggggggc ggagcctatg gaaaaacgcc agcaacgcgg    7500
cctttttacg gttcctggcc ttttgctggc cttttgctca catgttcttt cctgcgttat    7560
cccctgattc tgtggataac cgtattaccg cctttgagtg agctgatacc gctcgccgca    7620
gccgaacgac cgagcgcagc gagtcagtga gcgaggaagc ggaagagcgc ccaatacgca    7680
aaccgcctct ccccgcgcgt tggccgattc attaatgcag ctgggctgca            7730
```

<210> SEQ ID NO 4
<211> LENGTH: 6460
<212> TYPE: DNA
<213> ORGANISM: Artificial
<220> FEATURE:

-continued

<223> OTHER INFORMATION: plasmid

<400> SEQUENCE: 4

```
gggggggggg ggggggggtt ggccactccc tctctgcgcg ctcgctcgct cactgaggcc      60
gggcgaccaa aggtcgcccg acgcccgggc tttgcccggg cggcctcagt gagcgagcga     120
gcgcgcagag agggagtggc caactccatc actaggggtt cctagatctg aattcggtac     180
ccgttacata acttacggta aatggcccgc ctggctgacc gcccaacgac ccccgcccat     240
tgacgtcaat aatgacgtat gttcccatag taacgccaat agggactttc cattgacgtc     300
aatgggtgga gtatttacgg taaactgccc acttggcagt acatcaagtg tatcatatgc     360
caagtacgcc ccctattgac gtcaatgacg gtaaatggcc cgcctggcat tatgcccagt     420
acatgacctt atgggacttt cctacttggc agtacatcta cgtattagtc atcgctatta     480
ccatggtgat gcggttttgg cagtacatca atgggcgtgg atagcggttt gactcacggg     540
gatttccaag tctccacccc attgacgtca atgggagttt gttttggcac caaaatcaac     600
gggactttcc aaaatgtcgt aacaactccg ccccattgac gcaaatgggc ggtaggcgtg     660
tacggtggga ggtctatata agcagagctc gtttagtgaa ccgtcagatc gcctggagac     720
gccatccacg ctgttttgac ctccatagaa gacaccggga ccgatccagc ctccggactc     780
tagaggatcc ggtactcgag gaactgaaaa accagaaagt taactggtaa gtttagtctt     840
tttgtctttt atttcaggtc ccggatccgg tggtggtgca aatcaaagaa ctgctcctca     900
gtggatgttg cctttacttc taggcctgta cggaagtgtt acttctgctc taaaagctgc     960
ggaattgtac ccgcggcccg ggatccaccg gccaccggta ttcgcagacc atggaggctg    1020
ttgctgttgc agccgctgtg ggcgtcttgc tgttggccgg tgccggggga gctgctggcg    1080
acgaggcaag ggaagctgca gctgtgcggg ctctcgtcgc aaggttgctg ggtccaggtc    1140
ccgctgctga ctttagtgtg tcagtggaga gggctttggc cgctaaacct ggcctggaca    1200
cctactccct gggtggaggt ggggctgccc gcgtgagggt gagaggctca acgggggtgg    1260
ctgctgcagc aggtctgcat aggtacctca gagacttctg cggatgccat gtcgcttgga    1320
gcggcagtca actgaggctg ccccggcccc tccctgccgt ccctgggaa cttacagaag     1380 ctactccaaa taggtacaga tattatcaaa atgtgtgtac gcagagttac agctttgtgt    1440
ggtgggactg ggcaaggtgg gagcgcgaaa tcgattggat ggccctcaac gggatcaatc    1500
tggccttggc atggtccgga caggaagcta tctggcagcg cgtgtatctg gctctcgggt    1560
tgactcaagc tgaaatcaac gagtttttca caggccccgc cttcctggcc tggggggcgga   1620 tgggtaatct tcatacttgg gacgggccac tgccccctc ttggcacatc aaacagttgt     1680
atctgcagca ccgcgtcctg gaccagatgc gcagcttcgg catgactccc gtcctgccgg    1740
ctttcgcagg gcacgtccca gaggcggtca cacgggtctt ccctcaggtg aatgtgacaa    1800
aaatgggatc atggggacat ttcaattgtt cttacagttg ttccttcctg ctggcacccg    1860
aagatcctat cttcccaatc ataggaagtc tctttctgcg cgagttgatt aaggagttcg    1920
gtactgatca catttatggc gctgatactt ttaacgaaat gcagcccccc tcttctgaac    1980
catcctatct tgctgccgca accactgccg tttatgaagc catgaccgcc gtggacactg    2040
aagccgtttg gcttctccaa ggttggctgt tccagcacca gcctcagttt tggggggccag   2100 ctcagataag agccgttctc ggcgctgtac ctcgcggaag actgctggtg cttgatttgt    2160
tcgcagagtc tcagccagtg tacacgagaa ccgcttcctt ccagggccag ccgtttattt    2220
ggtgtatgct tcacaatttt ggcggaaatc atgggctgtt cggtgccctg gaggccgtca    2280
```

-continued

```
atgggggacc tgaggctgca agattgttcc caaactcaac catggtgggg accggaatgg   2340 caccegaagg cattagccag aatgaggtcg tctacagtct gatggcggaa ttggggtggc   2400
ggaaggaccc cgtgccagat ctcgccgcct gggtgactag ctttgccgcc cgccgctatg   2460
gagtgagcca tcctgatgca ggcgcagcct ggcggctgtt gcttcgatca gtatacaatt   2520
gttcaggaga ggcctgccgg gggcacaata ggagcccact ggtaaggagg cccagcctgc   2580
agatgaacac ctctatctgg tacaacagaa gcgatgtttt cgaggcttgg agacttctcc   2640
ttacatctgc ccctagcttg gccaccagtc cagccttccg atatgatctg ctggacctca   2700
cccgacaggc cgtgcaggaa ctggtctctc tctactatga agaggccaga tcagcttacc   2760
tctctaaaga actggcctcc ctcttgcgag caggaggcgt cctggcatat gagctgctcc   2820
ctgcactgga cgaggtactg gcatctgatt cccgattcct gctcgggtca tggctggagc   2880
aagcccgagc agcggctgta agcgaggctg aagcagactt ctatgaacaa aatagtaggt   2940
atcaactgac tctgtggggt ccagagggga atatcctgga ctacgcgaac aaacagttgg   3000
cgggcctggt ggccaactac tacacccctc ggtggagatt gtttttggag gcgctggtgg   3060
attcagtcgc acagggggatt ccgtttcagc aacatcagtt tgacaagaac gtctttcagc   3120
tggaacaggc ttttgtgctt tctaagcagc gctacccttc tcagccaaga ggcgataccg   3180
ttgacctcgc gaagaaaatc tttctcaagt actatcccag atgggtggcc ggatcatggt   3240
aggtcgaccc tcgactagag ctcgctgatc agcctcgact gtgccttcta gttgccagcc   3300
atctgttgtt tgcccctccc ccgtgccttc cttgaccctg gaaggtgcca ctcccactgt   3360
cctttcctaa taaaatgagg aaattgcatc gcattgtctg agtaggtgtc attctattct   3420
ggggggtggg gtggggcagg acagcaaggg ggaggattgg gaagacaata gcaggcatgc   3480
tggggagaga tctaggaacc cctagtgatg gagttggcca ctccctctct gcgcgctcgc   3540
tcgctcactg aggccgcccg ggcaaagccc gggcgtcggg cgacctttgg tcgcccggcc   3600
tcagtgagcg agcgagcgcg cagagaggga gtggccaacc ccccccccc ccccctgca   3660 gccagctggc gtaatagcga agaggcccgc accgatcgcc cttcccaaca gttgcgtagc   3720
ctgaatggcg aatggcgcga cgcgccctgt agcggcgcat taagcgcggc gggtgtggtg   3780
gttacgcgca gcgtgaccgc tacacttgcc agcgccctag cgcccgctcc tttcgctttc   3840
ttcccttcct ttctcgccac gttcgccggc tttccccgtc aagctctaaa tcggggggctc   3900 cctttagggt tccgatttag tgctttacgg cacctcgacc ccaaaaaact tgattagggt   3960
gatggttcac gtagtgggcc atcgccctga tagacggttt ttcgcccttt gacgttggag   4020
tccacgttct ttaatagtgg actcttgttc caaactggaa caacactcaa ccctatctcg   4080
gtctattctt ttgatttata agggattttg ccgatttcgg cctattggtt aaaaaatgag   4140
ctgatttaac aaaaatttaa cgcgaatttt aacaaaatat taacgtttac aatttcctga   4200
tgcggtattt tctccttacg catctgtgcg gtatttcaca ccgcatatgg tgcactctca   4260
gtacaatctg ctctgatgcc gcatagttaa gccagccccg acacccgcca cacccgctg   4320 acgcgccctg acgggcttgt ctgctcccgg catccgctta cagacaagct gtgaccgtct   4380
ccgggagctg catgtgtcag aggttttcac cgtcatcacc gaaacgcgcg agacgaaagg   4440
gcctcgtgat acgcctattt ttataggtta atgtcatgat aataatggtt cttagacgt   4500 caggtggcac ttttcgggga atgtgcgcg gaacccctat ttgtttattt ttctaaatac   4560
attcaaatat gtatccgctc atgagacaat aaccctgata aatgcttcaa taatattgaa   4620
```

-continued

```
aaaggaagag tatgagtatt caacatttcc gtgtcgccct tattcccttt tttgcggcat    4680
tttgccttcc tgtttttgct cacccagaaa cgctggtgaa agtaaaagat gctgaagatc    4740
agttgggtgc acgagtgggt tacatcgaac tggatctcaa cagcggtaag atccttgaga    4800
gttttcgccc cgaagaacgt tttccaatga tgagcacttt taaagttctg ctatgtggcg    4860
cggtattatc ccgtattgac gccgggcaag agcaactcgg tcgccgcata cactattctc    4920
agaatgactt ggttgagtac tcaccagtca cagaaaagca tcttacggat ggcatgacag    4980
taagagaatt atgcagtgct gccataacca tgagtgataa cactgcggcc aacttacttc    5040
tgacaacgat cggaggaccg aaggagctaa ccgctttttt gcacaacatg ggggatcatg    5100
taactcgcct tgatcgttgg gaaccggagc tgaatgaagc cataccaaac gacgagcgtg    5160
acaccacgat gcctgtagca atggcaacaa cgttgcgcaa actattaact ggcgaactac    5220
ttactctagc ttcccggcaa caattaatag actggatgga ggcggataaa gttgcaggac    5280
cacttctgcg ctcggccctt ccggctggct ggtttattgc tgataaatct ggagccggtg    5340
agcgtgggtc tcgcggtatc attgcagcac tggggccaga tggtaagccc tcccgtatcg    5400
tagttatcta cacgacgggg agtcaggcaa ctatgacctt ccagggtcaa ggaagctgtc    5460
agaccaagtt tactcatata tactttagat tgatttaaaa cttcattttt aatttaaaag    5520
gatctaggtg aagatccttt ttgataatct catgaccaaa atcccttaac gtgagttttc    5580
gttccactga gcgtcagacc ccgtagaaaa gatcaaagga tcttcttgag atcctttttt    5640
tctgcgcgta atctgctgct tgcaaacaaa aaaaccaccg ctaccagcgg tggtttgttt    5700
gccggatcaa gagctaccaa ctctttttcc gaaggtaact ggcttcagca gagcgcagat    5760
accaaatact gtccttctag tgtagccgta gttaggccac cacttcaaga actctgtagc    5820
accgcctaca tacctcgctc tgctaatcct gttaccagtg gctgctgcca gtggcgataa    5880
gtcgtgtctt accgggttgg actcaagacg atagttaccg gataaggcgc agcggtcggg    5940
ctgaacgggg ggttcgtgca cacagcccag cttggagcga acgacctaca ccgaactgag    6000
atacctacag cgtgagcatt gagaaagcgc cacgcttccc gaagggagaa aggcggacag    6060
gtatccggta agcggcaggg tcggaacagg agagcgcacg agggagcttc caggggggaaa    6120 cgcctggtat ctttatagtc ctgtcgggtt tcgccacctc tgacttgagc gtcgattttt    6180
gtgatgctcg tcaggggggc ggagcctatg gaaaaacgcc agcaacgcgg cctttttacg    6240
gttcctggcc ttttgctggc cttttgctca catgttcttt cctgcgttat cccctgattc    6300
tgtggataac cgtattaccg cctttgagtg agctgatacc gctcgccgca gccgaacgac    6360
cgagcgcagc gagtcagtga gcgaggaagc ggaagagcgc ccaatacgca aaccgcctct    6420
ccccgcgcgt tggccgattc attaatgcag ctgggctgca                          6460
```

AAV-NAGLU VECTORS FOR TREATMENT OF MUCOPOLYSACCHARIDOSIS IIIB

STATEMENT OF PRIORITY

This application is a 35 U.S.C. § 371 national phase application of PCT Application PCT/US2021/023383 filed Mar. 22, 2021, which claims the benefit of U.S. Provisional Application Ser. No. 62/993,266, filed Mar. 23, 2020, the entire contents of each of which are incorporated by reference herein.

FIELD OF THE INVENTION

This invention relates to viral vectors for delivery of α-N-acetylglucosaminidase (NAGLU) to a subject. In some aspects the NAGLU sequence is optimized for expression in human cells. The invention further relates to methods of using the vector to increase secretion of NAGLU from a cell and for treatment and prevention of mucopolysaccharidosis IIIB.

BACKGROUND OF THE INVENTION

Mucopolysaccharidosis (MPS) IIIB (also called Sanfilippo syndrome type B) is a devastating autosomal recessive lysosomal storage disease (LSD), caused by defects in the gene encoding α-N-acetylglucosaminidase (NAGLU), a lysosomal enzyme essential for the degradation of heparan sulfates (HS), a class of biologically important glycosaminoglycans (GAGs). The lack of NAGLU activity results in the accumulation of undegraded and/or partially degraded HS in lysosomes in cells of virtually all organs. Cells in the central nervous system (CNS) are particularly affected, resulting in severe progressive neurological manifestations that lead to high morbidity and premature death (Neufeld et al., in *The metabolic & molecular basis of inherited disease* (eds C. R. Scriver, A. L. Beaudet, W. S. Sly, & D. Valle) 3421-3452 (McGraw-Hill, 2001); Weber et al., *Eur. J. Hum. Genet.* 7:34-44 (1999)). Infants with MPS IIIB appear normal at birth, but after 1-2 years of relatively normal development, progressive developmental delay and severe neurological disorders ensue (Valstar et al., *J. Inherit. Metab. Dis.* doi:10.1007/s10545-008-0838-5 (2008)). Somatic manifestations of MPS IIIB occur in all patients, but are mild relative to other forms of MPS. The majority of MPS IIIB patients are diagnosed at age 3-6 years when they have developed profound neurological disorders. Deaths occur typically in teenage years. No treatment is currently available for MPS IIIB (Valayannopoulos et al., *Rheumatology (Oxford)* 50 Suppl 5, v49-59, doi:ker396 [pii] 10.1093/rheumatology/ker396 (2011)). Therapies have been limited to supportive care. Therefore, there is urgent unmet medical need for MPS IIIB.

Gene therapy targeting the root cause is ideal for treating MPS IIIB, if broadly delivered to CNS and peripheral tissues, because of the potential for long-term endogenous production of recombinant enzymes. The by-stander effects of NAGLU enzyme allow optimal benefits without the need to transduce every cell (Neufeld et al., *Ann. NY Acad. Sci.* 179:580-587 (1971)). Among the gene delivery strategies, recombinant adeno-associated viral (rAAV) vector is an ideal tool for this application because it is safe with demonstrated long-term expression in the CNS and periphery (Foust et al., *Nature Biotechnol.* 27:59-65 (2009)). The demonstrated trans-blood brain barrier (BBB)-neurotropic AAV9 (Foust et al., *Nature Biotechnol.* 27:59-65 (2009);

Zincarelli et al., *Mol. Ther.* 16:1073-1080 (2008); Duque et al., *Mol. Ther.* 17:1187-1196, doi:mt200971 [pii] 10.1038/mt.2009.71 (2009)) has offered a great gene delivery tool for the treatment of monogenic diseases with neurological manifestations. Previously, the inventors developed a gene therapy product using rAAV9 vector to deliver the human NAGLU gene (hNAGLU) cDNA driven by the CMV promoter via systemic delivery, leading to the IND approval for a Phase I/II gene therapy clinical trial in patients with MPS IIIB (NCT03315182) (Fu et al., *Mol. Ther.* 19:1025-1033, doi:mt201134 [pii]10.1038/mt.2011.34 (2011); Meadows et al., *Human Gene Ther. Clin. Dev.* 26:228-242, doi:10.1089/humc.2015.132 (2015); Murrey et al., *Human Gene Ther. Clin. Dev.* 25:72-84, doi:10.1089/humc.2013.208 (2014)).

The present invention addresses unmet needs by providing improved therapeutic efficacy. The invention provides improved viral vectors for expression of NAGLU in the CNS and methods for treating or preventing MPS IIIB.

SUMMARY OF THE INVENTION

This invention is based on the finding that the use of AAV vectors comprising a nucleic acid encoding NAGLU that is codon-optimized for expression in human cells provides an unexpected increase in both expression and secretion of NAGLU. These vectors can be used advantageously for treatment of MPS IIIB as the treatment may be more effective than previous vectors for the dual reasons of enhanced expression levels in infected cells and increased bystander effect in non-infected cells due to enhanced secretion.

Thus, one aspect of the invention relates to a recombinant nucleic acid comprising a sequence encoding human α-N-acetylglucosaminidase (NAGLU) that is codon-optimized for expression in human cells, wherein the recombinant nucleic acid comprises a nucleotide sequence at least 90% identical to SEQ ID NO:1.

Another aspect of the invention relates to an AAV vector genome comprising the nucleic acid of the invention, an AAV particle comprising the AAV vector genome, and a pharmaceutical composition comprising the AAV particle.

A further aspect of the invention relates to a method of producing a recombinant AAV particle comprising an AAV capsid, the method comprising: providing a cell in vitro with an AAV Cap and AAV Rep coding sequences, the AAV vector genome of the invention, and helper functions for generating a productive AAV infection; and allowing assembly of the recombinant AAV particle comprising the AAV capsid and encapsidating the AAV vector genome.

An additional aspect of the invention relates to a method of expressing NAGLU in a cell, comprising contacting the cell with an effective amount of an AAV particle of the invention, thereby expressing NAGLU in the cell.

Another aspect of the invention relates to a method of increasing secretion of NAGLU from a cell, comprising contacting the cell with an effective amount of the AAV particle of the invention, thereby increasing secretion of NAGLU from the cell relative to the secretion of NAGLU after contacting the cell with an AAV particle comprising a nucleic acid comprising the wild-type sequence for NAGLU.

A further aspect of the invention relates to a method of delivering NAGLU to a subject, comprising administering to the subject an effective amount of the AAV particle or the pharmaceutical formulation of the invention, thereby delivering NAGLU to the subject.

An additional aspect of the invention relates to a method of treating or delaying the onset of mucopolysaccharidosis IIIB (MPS IIIB) in a subject in need thereof, comprising administering to the subject a therapeutically effective amount of the AAV particle or the pharmaceutical formulation of the invention, thereby treating or delaying the onset of MPS IIIB in the subject.

These and other aspects of the invention are set forth in more detail in the description of the invention below.

BRIEF DESCRIPTION OF THE DRAWINGS

FIG. 1 shows the schematic structure of rAAV-hNAGLU$^{op}$ (PP viral vector genomes. ITR: AAV2 terminal repeat; SD: SV40 splicing signal; hNAGLU$^{op}$: codon-optimized human α-N-acetylglucosaminidase cDNA; PA: SV40 polyadenylation signal; CBA: chicken β actin promoter with CMV enhancer; CMV: human CMV immediate early enhancer/promoter.

FIGS. 2A-2C show AAV-hNAGLU$^{op}$ mediated effective expression and enhanced secretion of rNAGLU in vitro. HEK 293 cells were transfected in duplicates with 1 μg plasmid of pAAV-CMV-hNAGLU (CMV-NAG), pAAV-CBA-hNAGLU$^{op}$ (CBA-NAG-op), or pAAV-CMV-hNAGLU$^{op}$ (CMV-NAG-op). Controls were non-transfected cells (NT). Cell lysates and media were assayed in duplicates for NAGLU activity at 48 h post transfection.

DETAILED DESCRIPTION OF THE INVENTION

Figures 3A, 3B, 3C:
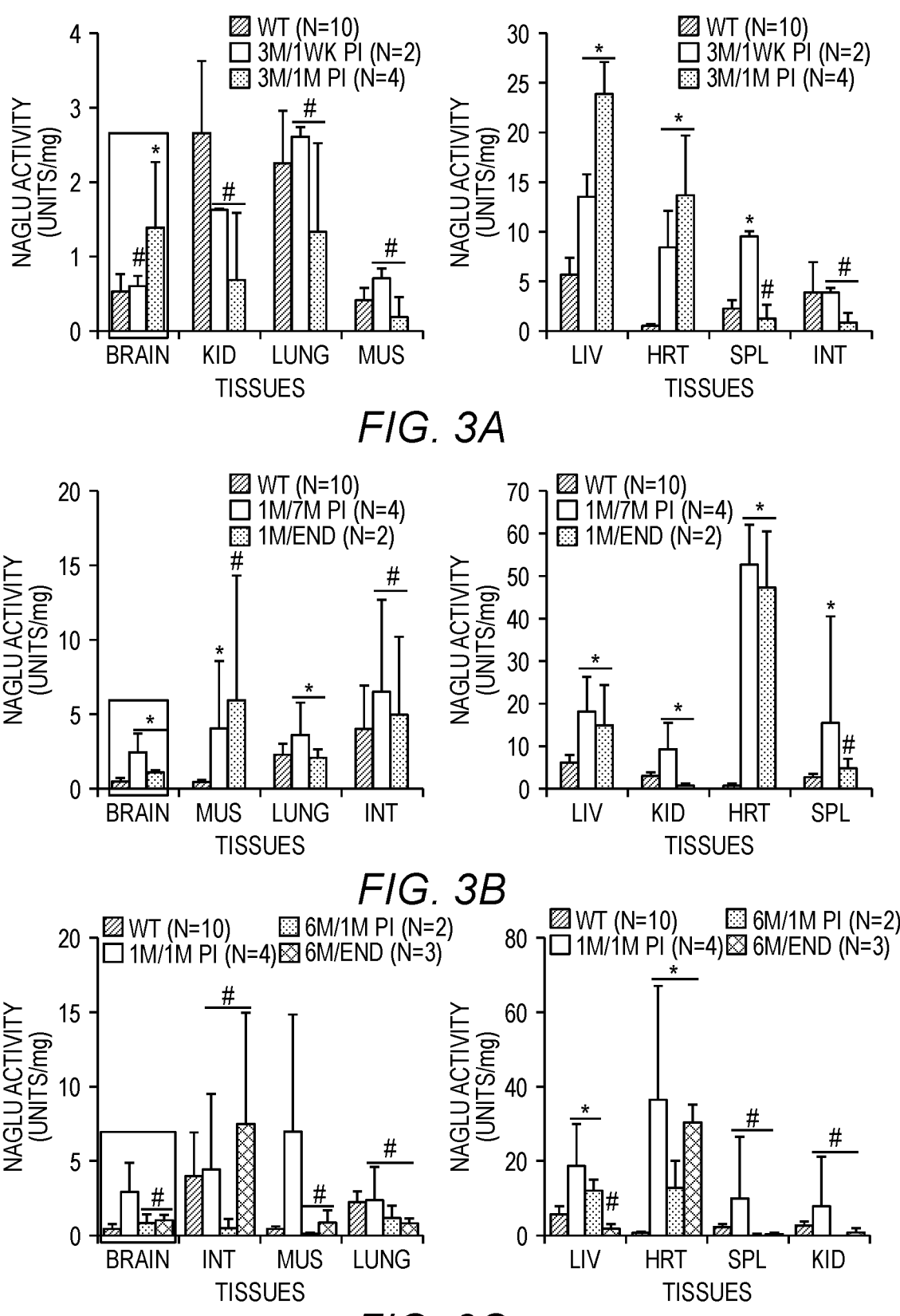
FIGS. 3A-3C show AAV9-mediated persistent restoration of NAGLU activity in the CNS and peripheral tissues in MPS IIIB mice following an IV vector delivery. MPS IIIB mice were treated at age 1 month (B, C), 3 months (A), or 6 months (C) with an IV injection of $1 \times 10^{13}$ vg/kg (B) or $2 \times 10^{13}$ vg/kg (A, C) rAAV9-CBA-hNAGLU$^{op}$. Tissues were assayed for NAGLU activity at 1 week post-injection (pi) (A), 1 month pi (A, C), 7 months pi (B) or endpoint (B, C). NAGLU activity is expressed as units/mg protein, 1 unit=nmol of 4 MU released/hr. There was no detectable NAGLU activity in tissues in non-treated MPS IIIB mice. m/m: Injection age/testing time. *: p<0.05 vs. WT; #: p>0.05 vs. WT.

The present invention will now be described with reference to the accompanying drawings, in which preferred embodiments of the invention are shown. This invention may, however, be embodied in different forms and should not be construed as limited to the embodiments set forth herein. Rather, these embodiments are provided so that this disclosure will be thorough and complete, and will fully convey the scope of the invention to those skilled in the art.

Unless otherwise defined, all technical and scientific terms used herein have the same meaning as commonly understood by one of ordinary skill in the art to which this invention belongs. The terminology used in the description of the invention herein is for the purpose of describing particular embodiments only and is not intended to be limiting of the invention. All publications, patent applications, patents, and other references mentioned herein are incorporated by reference in their entirety.

Nucleotide sequences are presented herein by single strand only, in the 5' to 3' direction, from left to right, unless specifically indicated otherwise. Nucleotides and amino acids are represented herein in the manner recommended by the IUPAC-IUB Biochemical Nomenclature Commission, or (for amino acids) by either the one-letter code, or the three letter code, both in accordance with 37 CFR § 1.822 and established usage. See, e.g., *Patent In User Manual,* 99-102 (November 1990) (U.S. Patent and Trademark Office).

Except as otherwise indicated, standard methods known to those skilled in the art may be used for the construction of recombinant parvovirus and AAV (rAAV) constructs, packaging vectors expressing the parvovirus Rep and/or Cap sequences, and transiently and stably transfected packaging cells. Such techniques are known to those skilled in the art. See, e.g., SAMBROOK et al., MOLECULAR CLONING: A LABORATORY MANUAL 2nd Ed. (Cold Spring Harbor, NY, 1989); AUSUBEL et al., CURRENT PROTOCOLS IN MOLECULAR BIOLOGY (Green Publishing Associates, Inc. and John Wiley & Sons, Inc., New York).

Moreover, the present invention also contemplates that in some embodiments of the invention, any feature or combination of features set forth herein can be excluded or omitted.

[To illustrate further, if, for example, the specification indicates that a particular amino acid can be selected from A, G, I, L and/or V, this language also indicates that the amino acid can be selected from any subset of these amino acid(s) for example A, G, I or L; A, G, I or V; A or G; only L; etc. as if each such subcombination is expressly set forth herein. Moreover, such language also indicates that one or more of the specified amino acids can be disclaimed. For example, in particular embodiments the amino acid is not A, G or I; is not A; is not G or V; etc. as if each such possible disclaimer is expressly set forth herein.

Definitions

The following terms are used in the description herein and the appended claims.

The singular forms "a" and "an" are intended to include the plural forms as well, unless the context clearly indicates otherwise.

Furthermore, the term "about," as used herein when referring to a measurable value such as an amount of the length of a polynucleotide or polypeptide sequence, dose, time, temperature, and the like, is meant to encompass variations of 20%, 10%, 5%, 1%, 0.5%, or even 0.1% of the specified amount.

Also as used herein, "and/or" refers to and encompasses any and all possible combinations of one or more of the associated listed items, as well as the lack of combinations when interpreted in the alternative ("or").

As used herein, the transitional phrase "consisting essentially of" is to be interpreted as encompassing the recited materials or steps "and those that do not materially affect the basic and novel characteristic(s)" of the claimed invention (e.g., rAAV replication). Thus, the term "consisting essentially of" as used herein should not be interpreted as equivalent to "comprising."

The term "consists essentially of" (and grammatical variants), as applied to a polynucleotide or polypeptide sequence of this invention, means a polynucleotide or polypeptide that consists of both the recited sequence (e.g., SEQ ID NO) and a total of ten or less (e.g., 1, 2, 3, 4, 5, 6, 7, 8, 9, or 10) additional nucleotides or amino acids on the 5' and/or 3' or N-terminal and/or C-terminal ends of the recited sequence such that the function of the polynucleotide or polypeptide is not materially altered. The total of ten or less additional nucleotides or amino acids includes the total number of additional nucleotides or amino acids on both ends added together. The term "materially altered," as applied to polynucleotides of the invention, refers to an increase or decrease in ability to express the encoded polypeptide of at least about 50% or more as compared to the expression level of a polynucleotide consisting of the recited sequence. The term "materially altered," as applied to polypeptides of the invention, refers to an increase or decrease in enzymatic activity of at least about 50% or more as compared to the activity of a polypeptide consisting of the recited sequence.

The term "parvovirus" as used herein encompasses the family Parvoviridae, including autonomously-replicating parvoviruses and dependoviruses. The autonomous parvoviruses include members of the genera Parvovirus, Erythrovirus, Densovirus, Iteravirus, and Contravirus. Exemplary autonomous parvoviruses include, but are not limited to, minute virus of mouse, bovine parvovirus, canine parvovirus, chicken parvovirus, feline panleukopenia virus, feline parvovirus, goose parvovirus, H1 parvovirus, muscovy duck parvovirus, snake parvovirus, and B19 virus. Other autonomous parvoviruses are known to those skilled in the art. See, e.g., FIELDS et al., VIROLOGY, volume 2, chapter 69 (4th ed., Lippincott-Raven Publishers).

The genus Dependovirus contains the adeno-associated viruses (AAV), including but not limited to, AAV type 1, AAV type 2, AAV type 3 (including types 3A and 3B), AAV type 4, AAV type 5, AAV type 6, AAV type 7, AAV type 8, AAV type 9, AAV type 10, AAV type 11, AAV type 12, AAV type 13, avian AAV, bovine AAV, canine AAV, goat AAV, snake AAV, equine AAV, and ovine AAV. See, e.g., FIELDS et al., VIROLOGY, volume 2, chapter 69 (4th ed., Lippincott-Raven Publishers); and Table 1.

As used herein, the term "adeno-associated virus" (AAV), includes but is not limited to, AAV type 1, AAV type 2, AAV type 3 (including types 3A and 3B), AAV type 4, AAV type 5, AAV type 6, AAV type 7, AAV type 8, AAV type 9, AAV type 10, AAV type 11, AAV type 12, AAV type 13, snake AAV, avian AAV, bovine AAV, canine AAV, equine AAV, ovine AAV, goat AAV, shrimp AAV, and any other AAV now known or later discovered. See, e.g., FIELDS et al., VIROLOGY, volume 2, chapter 69 (4th ed., Lippincott-Raven Publishers). A number of relatively new AAV serotypes and clades have been identified (See, e.g., Gao et al., (2004) *J. Virol.* 78:6381; Moris et al., (2004) *Virol.* 33-:375; and Table 1).

The parvovirus vectors, particles, and genomes of the present invention can be from, but are not limited to, AAV. The genomic sequences of various serotypes of AAV and the autonomous parvoviruses, as well as the sequences of the native ITRs, Rep proteins, and capsid subunits are known in the art. Such sequences may be found in the literature or in public databases such as GenBank. See, e.g., GenBank Accession Numbers NC_002077, NC_001401, NC_001729, NC_001863, NC_001829, NC_001862, NC_000883, NC_001701, NC_001510, NC_006152, NC_006261, AF063497, U89790, AF043303, AF028705, AF028704, J02275, J01901, J02275, X01457, AF288061, AH009962, AY028226, AY028223, AY631966, AX753250, EU285562, NC_001358, NC_001540, AF513851, AF513852 and AY530579; the disclosures of which are incorporated by reference herein for teaching parvovirus and AAV nucleic acid and amino acid sequences. See also, e.g., Bantel-Schaal et al., (1999) *J. Virol.* 73: 939; Chiorini et al., (1997) *J. Virol.* 71:6823; Chiorini et al., (1999) *J Virol.* 73:1309; Gao et al., (2002) *Proc. Nat. Acad. Sci. USA* 99:11854; Moris et al., (2004) *Virol.* 33-:375-383; Mori et al., (2004) *Virol.* 330: 375; Muramatsu et al., (1996) *Virol.* 221:208; Ruffing et al., (1994) *J. Gen. Virol.* 75:3385; Rutledge et al., (1998) *J. Virol.* 72:309; Schmidt et al., (2008) *J. Virol.* 82:8911; Shade et al., (1986) *J Virol.* 58:921; Srivastava et al., (1983) *J. Virol.* 45:555; Xiao et al., (1999) *J. Virol.* 73:3994; international patent publications WO 00/28061, WO 99/61601, WO 98/11244; and U.S. Pat. No. 6,156,303; the disclosures of which are incorporated by reference herein for teaching parvovirus and AAV nucleic acid and amino acid sequences. See also Table 1. An early description of the AAV1, AAV2 and AAV3 ITR sequences is provided by Xiao, X., (1996), "Characterization of Adeno-associated virus (AAV) DNA replication and integration," Ph.D. Dissertation, University of Pittsburgh, Pittsburgh, PA (incorporated herein in its entirety).

The term "tropism" as used herein refers to entry of the virus into the cell, optionally and preferably followed by expression (e.g., transcription and, optionally, translation) of sequences carried by the viral genome in the cell, e.g., for a recombinant virus, expression of the heterologous nucleotide sequences(s). Those skilled in the art will appreciate that transcription of a heterologous nucleic acid sequence from the viral genome may not be initiated in the absence of trans-acting factors, e.g., for an inducible promoter or otherwise regulated nucleic acid sequence. In the case of AAV, gene expression from the viral genome may be from a stably integrated provirus, from a non-integrated episome, as well as any other form in which the virus may take within the cell.

As used herein, "transduction" of a cell by parvovirus or AAV refers to parvovirus/AAV-mediated transfer of genetic material into the cell. See, e.g., FIELDS et al., VIROLOGY, volume 2, chapter 69 (3d ed., Lippincott-Raven Publishers).

The terms "5' portion" and "3' portion" are relative terms to define a spatial relationship between two or more elements. Thus, for example, a "3' portion" of a polynucleotide indicates a segment of the polynucleotide that is downstream of another segment. The term "3' portion" is not intended to indicate that the segment is necessarily at the 3' end of the polynucleotide, or even that it is necessarily in the 3' half of the polynucleotide, although it may be. Likewise, a "5' portion" of a polynucleotide indicates a segment of the polynucleotide that is upstream of another segment. The term "5' portion" is not intended to indicate that the segment is necessarily at the 5' end of the polynucleotide, or even that it is necessarily in the 5' half of the polynucleotide, although it may be.

TABLE 1

| AAV Serotypes/Isolates | GenBank Accession Number |
|---|---|
| Clonal Isolates | |
| Avian AAV ATCC VR-865 | AY186198, AY629583, NC_004828 |
| Avian AAV strain DA-1 | NC_006263, AY629583 |
| Bovine AAV | NC_005889, AY388617 |
| AAV4 | NC_001829 |

TABLE 1-continued

| AAV Serotypes/Isolates | GenBank Accession Number |
|---|---|
| AAV5 | AY18065, AF085716 |
| Rh34 | AY243001 |
| Rh33 | AY243002 |
| Rh32 | AY243003 |
| AAV10 | AY631965 |
| AAV11 | AY631966 |
| AAV12 | DQ813647 |
| AAV13 | EU285562 |
| Clade A | |
| AAV1 | NC_002077, AF063497 |
| AAV6 | NC_001862 |
| Hu.48 | AY530611 |
| Hu 43 | AY530606 |
| Hu 44 | AY530607 |
| Hu 46 | AY530609 |
| Clade B | |
| Hu19 | AY530584 |
| Hu20 | AY530586 |
| Hu23 | AY530589 |
| Hu22 | AY530588 |
| Hu24 | AY530590 |
| Hu21 | AY530587 |
| Hu27 | AY530592 |
| Hu28 | AY530593 |
| Hu29 | AY530594 |
| Hu63 | AY530624 |
| Hu64 | AY530625 |
| Hu13 | AY530578 |
| Hu56 | AY530618 |
| Hu57 | AY530619 |
| Hu49 | AY530612 |
| Hu58 | AY530620 |
| Hu34 | AY530598 |
| Hu35 | AY530599 |
| AAV2 | NC_001401 |
| Hu45 | AY530608 |
| Hu47 | AY530610 |
| Hu51 | AY530613 |
| Hu52 | AY530614 |
| Hu T41 | AY695378 |
| Hu S17 | AY695376 |
| Hu T88 | AY695375 |
| Hu T71 | AY695374 |
| Hu T70 | AY695373 |
| Hu T40 | AY695372 |
| Hu T32 | AY695371 |
| Hu T17 | AY695370 |
| Hu LG15 | AY695377 |
| Clade C | |
| AAV 3 | NC_001729 |
| AAV 3B | NC_001863 |
| Hu9 | AY530629 |
| Hu10 | AY530576 |
| Hu11 | AY530577 |
| Hu53 | AY530615 |
| Hu55 | AY530617 |
| Hu54 | AY530616 |
| Hu7 | AY530628 |
| Hu18 | AY530583 |
| Hu15 | AY530580 |
| Hu16 | AY530581 |
| Hu25 | AY530591 |
| Hu60 | AY530622 |
| Ch5 | AY243021 |

TABLE 1-continued

| AAV Serotypes/Isolates | GenBank Accession Number |
|---|---|
| Hu3 | AY530595 |
| Hu1 | AY530575 |
| Hu4 | AY530602 |
| Hu2 | AY530585 |
| Hu61 | AY530623 |
| Clade D | |
| Rh62 | AY530573 |
| Rh48 | AY530561 |
| Rh54 | AY530567 |
| Rh55 | AY530568 |
| Cy2 | AY243020 |
| AAV7 | AF513851 |
| Rh35 | AY243000 |
| Rh37 | AY242998 |
| Rh36 | AY242999 |
| Cy6 | AY243016 |
| Cy4 | AY243018 |
| Cy3 | AY243019 |
| Cy5 | AY243017 |
| Rh13 | AY243013 |
| Clade E | |
| Rh38 | AY530558 |
| Hu66 | AY530626 |
| Hu42 | AY530605 |
| Hu67 | AY530627 |
| Hu40 | AY530603 |
| Hu41 | AY530604 |
| Hu37 | AY530600 |
| Rh40 | AY530559 |
| Rh2 | AY243007 |
| Bb1 | AY243023 |
| Bb2 | AY243022 |
| Rh10 | AY243015 |
| Hu17 | AY530582 |
| Hu6 | AY530621 |
| Rh25 | AY530557 |
| Pi2 | AY530554 |
| Pi1 | AY530553 |
| Pi3 | AY530555 |
| Rh57 | AY530569 |
| Rh50 | AY530563 |
| Rh49 | AY530562 |
| Hu39 | AY530601 |
| Rh58 | AY530570 |
| Rh61 | AY530572 |
| Rh52 | AY530565 |
| Rh53 | AY530566 |
| Rh51 | AY530564 |
| Rh64 | AY530574 |
| Rh43 | AY530560 |
| AAV8 | AF513852 |
| Rh8 | AY242997 |
| Rh1 | AY530556 |
| Clade F | |
| AAV9 (Hu14) | AY530579 |
| Hu31 | AY530596 |
| Hu32 | AY530597 |

As used herein, the term "polypeptide" encompasses both peptides and proteins, unless indicated otherwise.

A "polynucleotide" is a sequence of nucleotide bases, and may be RNA, DNA or DNA-RNA hybrid sequences (including both naturally occurring and non-naturally occurring nucleotides), and can be either single or double stranded DNA sequences.

The term "codon-optimized," as used herein, refers to a gene coding sequence that has been optimized to increase expression by substituting one or more codons normally present in a coding sequence (for example, in a wildtype sequence, including, e.g., a coding sequence for NAGLU)

with a codon for the same (synonymous) amino acid. In this manner, the protein encoded by the gene is identical, but the underlying nucleobase sequence of the gene or corresponding mRNA is different. In some embodiments, the optimization substitutes one or more rare codons (that is, codons for tRNA that occur relatively infrequently in cells from a particular species) with synonymous codons that occur more frequently to improve the efficiency of translation. For example, in human codon-optimization one or more codons in a coding sequence are replaced by codons that occur more frequently in human cells for the same amino acid. Codon optimization can also increase gene expression through other mechanisms that can improve efficiency of transcription and/or translation. Strategies include, without limitation, increasing total GC content (that is, the percent of guanines and cytosines in the entire coding sequence), decreasing CpG content (that is, the number of CG or GC dinucleotides in the coding sequence), removing cryptic splice donor or acceptor sites, and/or adding or removing ribosomal entry sites, such as Kozak sequences. Desirably, a codon-optimized gene exhibits improved protein expression, for example, the protein encoded thereby is expressed at a detectably greater level in a cell compared with the level of expression of the protein provided by the wildtype gene in an otherwise similar cell.

The term "sequence identity," as used herein, has the standard meaning in the art. As is known in the art, a number of different programs can be used to identify whether a polynucleotide or polypeptide has sequence identity or similarity to a known sequence. Sequence identity or similarity may be determined using standard techniques known in the art, including, but not limited to, the local sequence identity algorithm of Smith & Waterman, *Adv. Appl. Math.* 2:482 (1981), by the sequence identity alignment algorithm of Needleman & Wunsch, *J. Mol. Biol.* 48:443 (1970), by the search for similarity method of Pearson & Lipman, *Proc. Natl. Acad. Sci. USA* 85:2444 (1988), by computerized implementations of these algorithms (GAP, BESTFIT, FASTA, and TFASTA in the Wisconsin Genetics Software Package, Genetics Computer Group, 575 Science Drive, Madison, WI), the Best Fit sequence program described by Devereux et al., *Nucl. Acid Res.* 12:387 (1984), preferably using the default settings, or by inspection.

An example of a useful algorithm is PILEUP. PILEUP creates a multiple sequence alignment from a group of related sequences using progressive, pairwise alignments. It can also plot a tree showing the clustering relationships used to create the alignment. PILEUP uses a simplification of the progressive alignment method of Feng & Doolittle, *J. Mol. Evol.* 35:351 (1987); the method is similar to that described by Higgins & Sharp, *CABIOS* 5:151 (1989).

Another example of a useful algorithm is the BLAST algorithm, described in Altschul et al., *J. Mol. Biol.* 215:403 (1990) and Karlin et al., *Proc. Natl. Acad. Sci. USA* 90:5873 (1993). A particularly useful BLAST program is the WU-BLAST-2 program which was obtained from Altschul et al., *Meth. Enzymol.,* 266:460 (1996); blast.wustl/edu/blast/README.html. WU-BLAST-2 uses several search parameters, which are preferably set to the default values. The parameters are dynamic values and are established by the program itself depending upon the composition of the particular sequence and composition of the particular database against which the sequence of interest is being searched; however, the values may be adjusted to increase sensitivity.

An additional useful algorithm is gapped BLAST as reported by Altschul et al., *Nucleic Acids Res.* 25:3389 (1997).

A percentage amino acid sequence identity value is determined by the number of matching identical residues divided by the total number of residues of the "longer" sequence in the aligned region. The "longer" sequence is the one having the most actual residues in the aligned region (gaps introduced by WU-Blast-2 to maximize the alignment score are ignored).

In a similar manner, percent nucleic acid sequence identity is defined as the percentage of nucleotide residues in the candidate sequence that are identical with the nucleotides in the polynucleotide specifically disclosed herein.

The alignment may include the introduction of gaps in the sequences to be aligned. In addition, for sequences which contain either more or fewer nucleotides than the polynucleotides specifically disclosed herein, it is understood that in one embodiment, the percentage of sequence identity will be determined based on the number of identical nucleotides in relation to the total number of nucleotides. Thus, for example, sequence identity of sequences shorter than a sequence specifically disclosed herein, will be determined using the number of nucleotides in the shorter sequence, in one embodiment. In percent identity calculations relative weight is not assigned to various manifestations of sequence variation, such as insertions, deletions, substitutions, etc.

In one embodiment, only identities are scored positively (+1) and all forms of sequence variation including gaps are assigned a value of "0," which obviates the need for a weighted scale or parameters as described below for sequence similarity calculations. Percent sequence identity can be calculated, for example, by dividing the number of matching identical residues by the total number of residues of the "shorter" sequence in the aligned region and multiplying by 100. The "longer" sequence is the one having the most actual residues in the aligned region.

As used herein, an "isolated" polynucleotide (e.g., an "isolated DNA" or an "isolated RNA") means a polynucleotide separated or substantially free from at least some of the other components of the naturally occurring organism or virus, for example, the cell or viral structural components or other polypeptides or nucleic acids commonly found associated with the polynucleotide.

Likewise, an "isolated" polypeptide means a polypeptide that is separated or substantially free from at least some of the other components of the naturally occurring organism or virus, for example, the cell or viral structural components or other polypeptides or nucleic acids commonly found associated with the polypeptide.

A "therapeutic polypeptide" is a polypeptide that may alleviate or reduce symptoms that result from an absence or defect in a protein in a cell or subject. Alternatively, a "therapeutic polypeptide" is one that otherwise confers a benefit to a subject, e.g., anti-cancer effects or improvement in transplant survivability.

As used herein, the term "modified," as applied to a polynucleotide or polypeptide sequence, refers to a sequence that differs from a wild-type sequence due to one or more deletions, additions, substitutions, or any combination thereof.

As used herein, by "isolate" or "purify" (or grammatical equivalents) a virus vector, it is meant that the virus vector is at least partially separated from at least some of the other components in the starting material.

By the terms "treat," "treating," or "treatment of" (and grammatical variations thereof) it is meant that the severity of the subject's condition is reduced, at least partially improved or stabilized and/or that some alleviation, mitigation, decrease or stabilization in at least one clinical symptom is achieved and/or there is a delay in the progression of the disease or disorder.

The terms "prevent," "preventing," and "prevention" (and grammatical variations thereof) refer to prevention and/or delay of the onset of a disease, disorder and/or a clinical symptom(s) in a subject and/or a reduction in the severity of the onset of the disease, disorder and/or clinical symptom(s) relative to what would occur in the absence of the methods of the invention. The prevention can be complete, e.g., the total absence of the disease, disorder and/or clinical symptom(s). The prevention can also be partial, such that the occurrence of the disease, disorder and/or clinical symptom(s) in the subject and/or the severity of onset is less than what would occur in the absence of the present invention.

A "treatment effective" amount as used herein is an amount that is sufficient to provide some improvement or benefit to the subject. Alternatively stated, a "treatment effective" amount is an amount that will provide some alleviation, mitigation, decrease or stabilization in at least one clinical symptom in the subject. Those skilled in the art will appreciate that the therapeutic effects need not be complete or curative, as long as some benefit is provided to the subject.

A "prevention effective" amount as used herein is an amount that is sufficient to prevent and/or delay the onset of a disease, disorder and/or clinical symptoms in a subject and/or to reduce and/or delay the severity of the onset of a disease, disorder and/or clinical symptoms in a subject relative to what would occur in the absence of the methods of the invention. Those skilled in the art will appreciate that the level of prevention need not be complete, as long as some benefit is provided to the subject.

The terms "heterologous nucleotide sequence" and "heterologous nucleic acid" are used interchangeably herein and refer to a sequence that is not naturally occurring in the virus. In some embodiments, the heterologous nucleic acid comprises an open reading frame that encodes a polypeptide or nontranslated RNA of interest (e.g., for delivery to a cell or subject).

As used herein, the terms "virus vector," "vector" or "gene delivery vector" refer to a virus (e.g., AAV) particle that functions as a nucleic acid delivery vehicle, and which comprises the vector genome (e.g., viral DNA [vDNA]) packaged within a virion. Alternatively, in some contexts, the term "vector" may be used to refer to the vector genome/vDNA alone or a plasmid.

The virus vectors of the invention can further be duplexed parvovirus particles as described in international patent publication WO 01/92551 (the disclosure of which is incorporated herein by reference in its entirety). Thus, in some embodiments, double stranded (duplex) genomes can be packaged.

A "rAAV vector genome" or "rAAV genome" is an AAV genome (i.e., vDNA) that comprises one or more heterologous nucleic acid sequences. rAAV vectors generally require only the 145 base ITR in cis to generate virus. All other viral sequences are dispensable and may be supplied in trans (Muzyczka (1992) *Curr. Topics Microbiol. Immunol.* 158: 97). Typically, the rAAV vector genome will only retain the one or more ITR sequence so as to maximize the size of the transgene that can be efficiently packaged by the vector. The structural and non-structural protein coding sequences may be provided in trans (e.g., from a vector, such as a plasmid, or by stably integrating the sequences into a packaging cell). In embodiments of the invention the rAAV vector genome comprises at least one ITR sequence (e.g., AAV ITR sequence), optionally two ITRs (e.g., two AAV ITRs), which typically will be at the 5' and 3' ends of the vector genome and flank the heterologous nucleic acid, but need not be contiguous thereto. The ITRs can be the same or different from each other.

The term "terminal repeat" or "TR" includes any viral terminal repeat or synthetic sequence that forms a hairpin structure and functions as an inverted terminal repeat (i.e., mediates the desired functions such as replication, virus packaging, integration and/or provirus rescue, and the like). The ITR can be an AAV ITR or a non-AAV ITR. For example, a non-AAV ITR sequence such as those of other parvoviruses (e.g., canine parvovirus, bovine parvovirus, mouse parvovirus, porcine parvovirus, human parvovirus B-19) or the SV40 hairpin that serves as the origin of SV40 replication can be used as an ITR, which can further be modified by truncation, substitution, deletion, insertion and/or addition. Further, the ITR can be partially or completely synthetic, such as the "double-D sequence" as described in U.S. Pat. No. 5,478,745 to Samulski et al.

Parvovirus genomes have palindromic sequences at both their 5' and 3' ends. The palindromic nature of the sequences leads to the formation of a hairpin structure that is stabilized by the formation of hydrogen bonds between the complementary base pairs. This hairpin structure is believed to adopt a "Y" or a "T" shape. See, e.g., FIELDS et al., VIROLOGY, volume 2, chapters 69 & 70 (4th ed., Lippincott-Raven Publishers).

An "AAV inverted terminal repeat" or "AAV ITR" may be from any AAV, including but not limited to serotypes 1, 2, 3a, 3b, 4, 5, 6, 7, 8, 9, 10, 11, or 13, snake AAV, avian AAV, bovine AAV, canine AAV, equine AAV, ovine AAV, goat AAV, shrimp AAV, or any other AAV now known or later discovered (see, e.g., Table 1). An AAV ITR need not have the native terminal repeat sequence (e.g., a native AAV ITR sequence may be altered by insertion, deletion, truncation and/or missense mutations), as long as the terminal repeat mediates the desired functions, e.g., replication, virus packaging, persistence, and/or provirus rescue, and the like.

The virus vectors of the invention can further be "targeted" virus vectors (e.g., having a directed tropism) and/or a "hybrid" parvovirus (i.e., in which the viral ITRs and viral capsid are from different parvoviruses) as described in international patent publication WO 00/28004 and Chao et al., (2000) Mol. Therapy 2:619.

Further, the viral capsid or genomic elements can contain other modifications, including insertions, deletions and/or substitutions.

The term "template" or "substrate" is used herein to refer to a polynucleotide sequence that may be replicated to produce the parvovirus viral DNA. For the purpose of vector production, the template will typically be embedded within a larger nucleotide sequence or construct, including but not limited to a plasmid, naked DNA vector, bacterial artificial chromosome (BAC), yeast artificial chromosome (YAC) or a viral vector (e.g., adenovirus, herpesvirus, Epstein-Barr Virus, AAV, baculoviral, retroviral vectors, and the like). Alternatively, the template may be stably incorporated into the chromosome of a packaging cell.

As used herein, parvovirus or AAV "Rep coding sequences" indicate the nucleic acid sequences that encode the parvoviral or AAV non-structural proteins that mediate viral replication and the production of new virus particles. The parvovirus and AAV replication genes and proteins have been described in, e.g., FIELDS et al., VIROLOGY, volume 2, chapters 69 & 70 (4th ed., Lippincott-Raven Publishers).

The "Rep coding sequences" need not encode all of the parvoviral or AAV Rep proteins. For example, with respect to AAV, the Rep coding sequences do not need to encode all four AAV Rep proteins (Rep78, Rep 68, Rep52 and Rep40), in fact, it is believed that AAV5 only expresses the spliced Rep68 and Rep40 proteins. In representative embodiments, the Rep coding sequences encode at least those replication proteins that are necessary for viral genome replication and packaging into new virions. The Rep coding sequences will generally encode at least one large Rep protein (i.e., Rep78/68) and one small Rep protein (i.e., Rep52/40). In particular embodiments, the Rep coding sequences encode the AAV Rep78 protein and the AAV Rep52 and/or Rep40 proteins. In other embodiments, the Rep coding sequences encode the Rep68 and the Rep52 and/or Rep40 proteins. In a still further embodiment, the Rep coding sequences encode the Rep68 and Rep52 proteins, Rep68 and Rep40 proteins, Rep78 and Rep52 proteins, or Rep78 and Rep40 proteins.

As used herein, the term "large Rep protein" refers to Rep68 and/or Rep78. Large Rep proteins of the claimed invention may be either wild-type or synthetic. A wild-type large Rep protein may be from any parvovirus or AAV, including but not limited to serotypes 1, 2, 3a, 3b, 4, 5, 6, 7, 8, 9, 10, 11, or 13, or any other AAV now known or later discovered (see, e.g., Table 1). A synthetic large Rep protein may be altered by insertion, deletion, truncation and/or missense mutations.

Those skilled in the art will further appreciate that it is not necessary that the replication proteins be encoded by the same polynucleotide. For example, for MVM, the NS-1 and NS-2 proteins (which are splice variants) may be expressed independently of one another. Likewise, for AAV, the p19 promoter may be inactivated and the large Rep protein(s) expressed from one polynucleotide and the small Rep protein(s) expressed from a different polynucleotide. Typically, however, it will be more convenient to express the replication proteins from a single construct. In some systems, the viral promoters (e.g., AAV p19 promoter) may not be recognized by the cell, and it is therefore necessary to express the large and small Rep proteins from separate expression cassettes. In other instances, it may be desirable to express the large Rep and small Rep proteins separately, i.e., under the control of separate transcriptional and/or translational control elements. For example, it may be desirable to control expression of the large Rep proteins, so as to decrease the ratio of large to small Rep proteins. In the case of insect cells, it may be advantageous to down-regulate expression of the large Rep proteins (e.g., Rep78/68) to avoid toxicity to the cells (see, e.g., Urabe et al., (2002) Human Gene Therapy 13:1935).

As used herein, the parvovirus or AAV "cap coding sequences" encode the structural proteins that form a functional parvovirus or AAV capsid (i.e., can package DNA and infect target cells). Typically, the cap coding sequences will encode all of the parvovirus or AAV capsid subunits, but less than all of the capsid subunits may be encoded as long as a functional capsid is produced. Typically, but not necessarily, the cap coding sequences will be present on a single nucleic acid molecule.

The capsid structure of autonomous parvoviruses and AAV are described in more detail in BERNARD N. FIELDS et al., VIROLOGY, volume 2, chapters 69 & 70 (4th ed., Lippincott-Raven Publishers).

Parvovirus Vectors Expressing NAGLU

The present invention provides parvovirus vectors, e.g., AAV vectors, that comprise a nucleotide sequence encoding NAGLU that is codon-optimized for expression in human cells and are capable of provided enhanced expression and secretion of NAGLU from cells infected with the vector.

One aspect of the invention relates to a recombinant nucleic acid comprising, consisting essentially of, or consisting of a nucleotide sequence encoding human α-N-acetylglucosaminidase (NAGLU) that is codon-optimized for expression in human cells. In certain embodiments, the nucleic acid is a non-naturally occurring sequence. In some embodiments, the nucleic acid comprises, consists essentially of, or consists of a nucleotide sequence that is at least 90% identical to SEQ ID NO:1, e.g., at least 91%, 92%, 93%, 94%, 95%, 96%, 97%, 98%, or 99% identical to SEQ ID NO:1. In some embodiments, the nucleic acid comprises, consists essentially of, or consists of the nucleotide sequence of SEQ ID NO:1. In some embodiments, the nucleic acid comprises at least 10 contiguous nucleotides of SEQ ID NO:1, e.g., at least 10, 25, 50, 100, 200, 300, 400, 500, 600, 700, 800, 900, 1000, 1100, 1200, 1300, 1400, 1500, 1600, 1700, 1800, 1900, 2000, 2100 or more.

SEQ ID NO: 1

```
   1 ATGGAGGCTG TTGCTGTTGC AGCCGCTGTG GGCGTCTTGC TGTTGGCCGG

51 TGCCGGGGGA GCTGCTGGCG ACGAGGCAAG GGAAGCTGCA GCTGTGCGGG

101 CTCTCGTCGC AAGGTTGCTG GGTCCAGGTC CCGCTGCTGA CTTTAGTGTG

151 TCAGTGGAGA GGGCTTTGGC CGCTAAACCT GGCCTGGACA CCTACTCCCT

201 GGGTGGAGGT GGGGCTGCCC GCGTGAGGGT GAGAGGCTCA ACGGGGGTGG

251 CTGCTGCAGC AGGTCTGCAT AGGTACCTCA GAGACTTCTG CGGATGCCAT

301 GTCGCTTGGA GCGGCAGTCA ACTGAGGCTG CCCCGGCCCC TCCCTGCCGT

351 CCCTGGGGAA CTTACAGAAG CTACTCCAAA TAGGTACAGA TATTATCAAA

401 ATGTGTGTAC GCAGAGTTAC AGCTTTGTGT GGTGGGACTG GGCAAGGTGG

451 GAGCGCGAAA TCGATTGGAT GGCCCTCAAC GGGATCAATC TGGCCTTGGC

501 ATGGTCCGGA CAGGAAGCTA TCTGGCAGCG CGTGTATCTG GCTCTCGGGT

551 TGACTCAAGC TGAAATCAAC GAGTTTTTCA CAGGCCCCGC CTTCCTGGCC

601 TGGGGGCGGA TGGGTAATCT TCATACTTGG GACGGGCCAC TGCCCCCCTC

651 TTGGCACATC AAACAGTTGT ATCTGCAGCA CCGCGTCCTG GACCAGATGC

701 GCAGCTTCGG CATGACTCCC GTCCTGCCGG CTTTCGCAGG GCACGTCCCA

751 GAGGCGGTCA CACGGGTCTT CCCTCAGGTG AATGTGACAA AAATGGGATC

801 ATGGGGACAT TTCAATTGTT CTTACAGTTG TTCCTTCCTG CTGGCACCCG

851 AAGATCCTAT CTTCCCAATC ATAGGAAGTC TCTTTCTGCG CGAGTTGATT

901 AAGGAGTTCG GTACTGATCA CATTTATGGC GCTGATACTT TTAACGAAAT

951 GCAGCCCCCC TCTTCTGAAC CATCCTATCT TGCTGCCGCA ACCACTGCCG

1001 TTTATGAAGC CATGACCGCC GTGGACACTG AAGCCGTTTG GCTTCTCCAA

1051 GGTTGGCTGT TCCAGCACCA GCCTCAGTTT TGGGGGCCAG CTCAGATAAG

1101 AGCCGTTCTC GGCGCTGTAC CTCGCGGAAG ACTGCTGGTG CTTGATTTGT

1151 TCGCAGAGTC TCAGCCAGTG TACACGAGAA CCGCTTCCTT CCAGGGCCAG

1201 CCGTTTATTT GGTGTATGCT TCACAATTTT GGCGGAAATC ATGGGCTGTT

1251 CGGTGCCCTG GAGGCGGTCA ATGGGGGACC TGAGGCTGCA AGATTGTTCC

1301 CAAACTCAAC CATGGTGGGG ACCGGAATGG CACCCGAAGG CATTAGCCAG

1351 AATGAGGTCG TCTACAGTCT GATGGCGGAA TTGGGGTGGC GGAAGGACCC

1401 CGTGCCAGAT CTCGCCGCCT GGGTGACTAG CTTTGCCGCC CGCCGCTATG

1451 GAGTGAGCCA TCCTGATGCA GGCGCAGCCT GGCGGCTGTT GCTTCGATCA

1501 GTATACAATT GTTCAGGAGA GGCCTGCCGG GGGCACAATA GGAGCCCACT

1551 GGTAAGGAGG CCCAGCCTGC AGATGAACAC CTCTATCTGG TACAACAGAA

1601 GCGATGTTTT CGAGGCTTGG AGACTTCTCC TTACATCTGC CCCTAGCTTG

1651 GCCACCAGTC CAGCCTTCCG ATATGATCTG CTGGACCTCA CCCGACAGGC
```

-continued

```
1701 CGTGCAGGAA CTGGTCTCTC TCTACTATGA AGAGGCCAGA TCAGCTTACC

1751 TCTCTAAAGA ACTGGCCTCC CTCTTGCGAG CAGGAGGCGT CCTGGCATAT

1801 GAGCTGCTCC CTGCACTGGA CGAGGTACTG GCATCTGATT CCCGATTCCT

1851 GCTCGGGTCA TGGCTGGAGC AAGCCCGAGC AGCGGCTGTA AGCGAGGCTG

1901 AAGCAGACTT CTATGAACAA AATAGTAGGT ATCAACTGAC TCTGTGGGGT

1951 CCAGAGGGGA ATATCCTGGA CTACGCGAAC AAACAGTTGG CGGGCCTGGT

2001 GGCCAACTAC TACACCCCTC GGTGGAGATT GTTTTTGGAG GCGCTGGTGG

2051 ATTCAGTCGC ACAGGGGATT CCGTTTCAGC AACATCAGTT TGACAAGAAC

2101 GTCTTTCAGC TGGAACAGGC TTTTGTGCTT TCTAAGCAGC GCTACCCTTC

2151 TCAGCCAAGA GGCGATACCG TTGACCTCGC GAAGAAAATC TTTCTCAAGT

2201 ACTATCCCAG ATGGGTGGCC GGATCATGGT AG
```

20

Methods of codon optimizing a nucleotide sequence to maximize expression in an organism are well known in the art and can be carried out using software available to the public. The wild-type sequence of human NAGLU is known in the art and shown in SEQ ID NO:2.

SEQ ID NO: 2

```
   1 ATGGAGGCGG TGGCGGTGGC CGCGGCGGTG GGGGTCCTTC TCCTGGCCGG

51 GGCCGGGGGC GCGGCAGGCG ACGAGGCCCG GGAGGCGGCG GCCGTGCGGG

101 CGCTCGTGGC CCGGCTGCTG GGGCCAGGCC CCGCGGCCGA CTTCTCCGTG

151 TCGGTGGAGC GCGCTCTGGC TGCCAAGCCG GGCTTGGACA CCTACAGCCT

201 GGGCGGCGGC GGCGCGGCGC GCGTGCGGGT GCGCGGCTCC ACGGGCGTGG

251 CGGCCGCCGC GGGGCTGCAC CGCTACCTGC GCGACTTCTG TGGCTGCCAC

301 GTGGCCTGGT CCGGCTCTCA GCTGCGCCTG CCGCGGCCAC TGCCAGCCGT

351 GCCGGGGGAG CTGACCGAGG CCACGCCCAA CAGGTACCGC TATTACCAGA

401 ATGTGTGCAC GCAAAGCTAC TCCTTCGTGT GGTGGGACTG GGCCCGCTGG

451 GAGCGAGAGA TAGACTGGAT GGCGCTGAAT GGCATCAACC TGGCACTGGC

501 CTGGAGCGGC CAGGAGGCCA TCTGGCAGCG GGTGTACCTG GCCTTGGGCC

551 TGACCCAGGC AGAGATCAAT GAGTTCTTTA CTGGTCCTGC CTTCCTGGCC

601 TGGGGGCGAA TGGGCAACCT GCACACCTGG GATGGCCCCC TGCCCCCCTC

651 CTGGCACATC AAGCAGCTTT ACCTGCAGCA CCGGGTCCTG GACCAGATGC

701 GCTCCTTCGG CATGACCCCA GTGCTGCCTG CATTCGCGGG GCATGTTCCC

751 GAGGCTGTCA CCAGGGTGTT CCCTCAGGTC AATGTCACGA AGATGGGCAG

801 TTGGGGCCAC TTTAACTGTT CCTACTCCTG CTCCTTCCTT CTGGCTCCGG

851 AAGACCCCAT ATTCCCCATC ATCGGGAGCC TCTTCCTGCG AGAGCTGATC

901 AAAGAGTTTG GCACAGACCA CATCTATGGG GCCGACACTT TCAATGAGAT

951 GCAGCCACCT TCCTCAGAGC CCTCCTACCT TGCCGCAGCC ACCACTGCCG

1001 TCTATGAGGC CATGACTGCA GTGGATACTG AGGCTGTGTG GCTGCTCCAA

1051 GGCTGGCTCT TCCAGCACCA GCCGCAGTTC TGGGGGCCCG CCCAGATCAG

1101 GGCTGTGCTG GGAGCTGTGC CCCGTGGCCG CCTCCTGGTT CTGGACCTGT

1151 TTGCTGAGAG CCAGCCTGTG TATACCGGCA CTGCCTCCTT CCAGGGCCAG
```

```
                                                    -continued
1201  CCCTTCATCT GGTGCATGCT GCACAACTTT GGGGGAAACC ATGGTCTTTT

1251  TGGAGCCCTA GAGGCTGTGA ACGGAGGCCC AGAAGCTGCC CGCCTCTTCC

1301  CCAACTCCAC CATGGTAGGC ACGGGCATGG CCCCCGAGGG CATCAGCCAG

1351  AACGAAGTGG TCTATTCCCT CATGGCTGAG CTGGGCTGGC GAAAGGACCC

1401  AGTGCCAGAT TTGGCAGCCT GGGTGACCAG CTTTGCCGCC CGGCGGTATG

1451  GGGTCTCCCA CCCGGACGCA GGGGCAGCGT GGAGGCTACT GCTCCGGAGT

1501  GTGTACAACT GCTCCGGGGA GGCCTGCAGG GGCCACAATC GTAGCCCGCT

1551  GGTCAGGCGG CCGTCCCTAC AGATGAATAC CAGCATCTGG TACAACCGAT

1601  CTGATGTGTT TGAGGCCTGG CGGCTGCTGC TCACATCTGC TCCCTCCCTG

1651  GCCACCAGCC CCGCCTTCCG CTACGACCTG CTGGACCTCA CTCGGCAGGC

1701  AGTGCAGGAG CTGGTCAGCT TGTACTATGA GGAGGCAAGA AGCGCCTACC

1751  TGAGCAAGGA GCTGGCCTCC CTGTTGAGGG CTGGAGGCGT CCTGGCCTAT

1801  GAGCTGCTGC CGGCACTGGA CGAGGTGCTG GCTAGTGACA GCCGCTTCTT

1851  GCTGGGCAGC TGGCTAGAGC AGGCCCGAGC AGCGGCAGTC AGTGAGGCCG

1901  AGGCCGATTT CTACGAGCAG AACAGCCGCT ACCAGCTGAC CTTGTGGGGG

1951  CCAGAAGGCA ACATCCTGGA CTATGCCAAC AAGCAGCTGG CGGGGTTGGT

2001  GGCCAACTAC TACACCCCTC GCTGGCGGCT TTTCCTGGAG GCGCTGGTTG

2051  ACAGTGTGGC CCAGGGCATC CCTTTCCAAC AGGACCAGTT TGACAAAAAT

2101  GTCTTCCAAC TGGAGCAGGC CTTCGTTCTC AGCAAGGAGA GGTACCCCAG

2151  CCAGCCGCGA GGAGACACTG TGGACCTGGC CAAGAAGATC TTCCTCAAAT

2201  ATTACCCCGG CTGGGTGGCC GGCTCTTGGT GA
```

The invention also provides a viral vector genome comprising the NAGLU nucleic acid of the invention. The viral vector genome may be a parvovirus vector genome, e.g., an AAV vector genome. In some embodiments, the AAV vector genome is a self-complementary AAV vector genome. The viral vector genome may further comprise a promoter operably linked to the NAGLU nucleic acid. In some embodiments, the promoter may be a constitutive promoter, e.g., the CBA promoter or the CMV promoter. In other embodiments, the promoter may be a tissue-specific or preferred promoter. The invention further provides a cell in vitro comprising the AAV vector genome of the invention, e.g., stably incorporated into the genome of the cell. The invention further provides a recombinant parvovirus particle (e.g., a recombinant AAV particle, e.g., an AAV9 particle) comprising the viral vector genome of the invention. Viral vectors and viral particles are discussed further below.

In some embodiments, the viral vector genome is encoded by a plasmid. Examples include, without limitation, a plasmid encoding rAAV9-CBA-hNAGLU$^{op}$ comprising, consisting essentially of, or consisting of SEQ ID NO:3 or a plasmid encoding rAAV9-CMV-hNAGLU$^{op}$ comprising, consisting essentially of, or consisting of SEQ ID NO:4, or a sequence at least 90% identical to SEQ ID NO:3 or 4, e.g., at least 91%, 92%, 93%, 94%, 95%, 96%, 97%, 98%, or 99% identical to SEQ ID NO:3 or 4.

```
pTR-CBA-NAGLU-op
                                                                    SEQ ID NO: 3

GGGGGGGGGGGGGGGGGGTTGGCCACTCCCTCTCTGCGCGCTCGCTCGCTCACTGAGGCCGGGCG

ACCAAAGGTCGCCCGACGCCCGGGCTTTGCCCGGGCGGCCTCAGTGAGCGAGCGAGCGCGCAGAG

AGGGAGTGGCCAACTCCATCACTAGGGGTTCCTAGATCTGGAAGCTGATCTTCAATATTGGCCATT

AGCCATATTATTCATTGGTTATATAGCATAAATCAATATTGGATATTGGCCATTGCATACGTTGTAT

CTATATCATAATATGTACATTTATATTGGCTCATGTCCAATATGACCGCCATGTTGGCATTGATTAT

TGACTAGTTATTAATAGTAATCAATTACGGGGTCATTAGTTCATAGCCCATATATGGAGTTCCGCG

TTACATAACTTACGGTAAATGGCCCGCCTGGCTGACCGCCCAACGACCCCCGCCCATTGACGTCAA

TAATGACGTATGTTCCCATAGTAACGCCAATAGGGACTTTCCATTGACGTCAATGGGTGGAGTATT

TACGGTAAACTGCCCACTTGGCAGTACATCAAGTGTATCATATGCCAAGTCCGCCCCCTATTGACG
```

-continued

TCAATGACGGTAAATGGCCCGCCTGGCATTATGCCCAGTACATGACCTTACGGGACTTTCCTACTT

GGCAGTACATCTACGTATTAGTCATCGCTATTACCATGGTCGAGGTGAGCCCCACGTTCTGCTTCA

CTCTCCCCATCTCCCCCCCCTCCCCACCCCCAATTTTGTATTTATTTATTTTTTAATTATTTTGTGCA

GCGATGGGGGCGGGGGGGGGGGGGGGGCGCGCGCCAGGCGGGGCGGGGCGGGGCGAGGGGCGG

GGCGGGGCGAGGCGGAGAGGTGCGGCGGCAGCCAATCAGAGCGGCGCGCTCCGAAAGTTTCCTTT

TATGGCGAGGCGGCGGCGGCGGCGGCCCTATAAAAAGCGAAGCGCGCGGCGGGCGGGAGTCGCT

GCGACGCTGCCTTCGCCCCGTGCCCCGCTCCGCCGCCGCCTCGCGCCGCCCGCCCCGGCTCTGACT

GACCGCGTTACTCCCACAGGTGAGCGGGCGGGACGGCCCTTCTCCTCCGGGCTGTAATTAGCGCTT

GGTTTAATGACGGCTTGTTTCTTTTCTGTGGCTGCGTGAAAGCCTTGAGGGGCTCCGGGAGGGCCC

TTTGTGCGGGGGGGAGCGGCTCGGGGGGTGCGTGCGTGTGTGTGCGTGGGGAGCGCCGCGTGC

GGCCCGCGCTGCCCGGCGGCTGTGAGCGCTGCGGGCGCGGCGCGGGGCTTTGTGCGCTCCGCAGT

GTGCGCGAGGGGAGCGCGGCCGGGGGCGGTGCCCCGCGGTGCGGGGGGGGCTGCGAGGGGAACA

AAGGCTGCGTGCGGGGTGTGTGCGTGGGGGGGTGAGCAGGGGGTATGGGCGCGGCGGTCGGGCT

GTAACCCCCCCCTGCACCCCCCTCCCCGAGTTGCTGAGCACGGCCCGGCTTCGGGTGCGGGGCTCC

GTACGGGGCGTGGCGCGGGGCTCGCCGTGCCGGGCGGGGGGTGGCGGCAGGTGGGGGTGCCGGG

CGGGGCGGGGCCGCCTCGGGCCGGGGAGGGCTCGGGGGAGGGGCGCGGCGGCCCCCGGAGCGCC

GGCGGCTGTCGAGGCGCGGCGAGCCGCAGCCATTGCCTTTTATGGTAATCGTGCGAGAGGGCGCA

GGGACTTACTTTGTCCCAAATCTGTGCGGAGCCGAAATCTGGGAGGCGCCGCCGCACCCCCTCTAG

CGGGCGCGGGGCGAAGCGGTGCGGCGCCGGCAGGAAGGAAATGGGCGGGGAGGGCCTTCGTGCG

TCGCCGCGCCGCCGTCCCCTTCTCCCTCTCCAGCCTCGGGGCTGTCCGCGGGGGGACGGCTGCCTT

CGGGGGGGGACGGGGCAGGGCGGGGTTCGGCTTCTGGCGTGTGACCGGCGGCTCTAGAGCCTCTGC

TAACCATGTTCATGCCTTCTTCTTTTTCCTACAGCTCCTGGGCAACGTGCTGGTTATTGTGCTGTCTC

ATCATTTTGGCAAAGAATTCGATAGGATCCGGTACTCGAGGAACTGAAAAACCAGAAAGTTAACT

GGTAAGTTTAGTCTTTTTGTCTTTTATTTCAGGTCCCGGATCCGGTGGTGGTGCAAATCAAAGAACT

GCTCCTCAGTGGATGTTGCCTTTACTTCTAGGCCTGTACGGAAGTGTTACTTCTGCTCTAAAAGCTG

CGGAATTGTACCCGCGGCCCGGGATCCACCGGCCACCGGtATTCgcAGACCATGGAGGCTGTTGCTG

TTGCAGCCGCTGTGGGCGTCTTGCTGTTGGCCGGTGCCGGGGGAGCTGCTGGCGACGAGGCAAGG

GAAGCTGCAGCTGTGCGGGCTCTCGTCGCAAGGTTGCTGGGTCCAGGTCCCGCTGCTGACTTTAGT

GTGTCAGTGGAGAGGGCTTTGGCCGCTAAACCTGGCCTGGACACCTACTCCCTGGGTGGAGGTGG

GGCTGCCCGCGTGAGGGTGAGAGGCTCAACGGGGGTGGCTGCTGCAGCAGGTCTGCATAGGTACC

TCAGAGACTTCTGCGGATGCCATGTCGCTTGGAGCGGCAGTCAACTGAGGCTGCCCCGGCCCCTCC

CTGCCGTCCCTGGGGAACTTACAGAAGCTACTCCAAATAGGTACAGATATTATCAAAATGTGTGTA

CGCAGAGTTACAGCTTTGTGTGGTGGGACTGGGCAAGGTGGGAGCGCGAAATCGATTGGATGGCC

CTCAACGGGATCAATCTGGCCTTGGCATGGTCCGGACAGGAAGCTATCTGGCAGCGCGTGTATCTG

GCTCTCGGGTTGACTCAAGCTGAAATCAACGAGTTTTTCACAGGCCCCGCCTTCCTGGCCTGGGGG

CGGATGGGTAATCTTCATACTTGGGACGGGCCACTGCCCCCCTCTTGGCACATCAAACAGTTGTAT

CTGCAGCACCGCGTCCTGGACCAGATGCGCAGCTTCGGCATGACTCCCGTCCTGCCGGCTTTCGCA

GGGCACGTCCCAGAGGCGGTCACACGGGTCTTCCCTCAGGTGAATGTGACAAAAATGGGATCATG

GGGACATTTCAATTGTTCTTACAGTTGTTCCTTCCTGCTGGCACCCGAAGATCCTATCTTCCCAATC

ATAGGAAGTCTCTTTCTGCGCGAGTTGATTAAGGAGTTCGGTACTGATCACATTTATGGCGCTGAT

-continued

```
ACTTTTAACGAAATGCAGCCCCCCTCTTCTGAACCATCCTATCTTGCTGCCGCAACCACTGCCGTTT

ATGAAGCCATGACCGCCGTGGACACTGAAGCCGTTTGGCTTCTCCAAGGTTGGCTGTTCCAGCACC

AGCCTCAGTTTTGGGGGCCAGCTCAGATAAGAGCCGTTCTCGGCGCTGTACCTCGCGGAAGACTGC

TGGTGCTTGATTTGTTCGCAGAGTCTCAGCCAGTGTACACGAGAACCGCTTCCTTCCAGGGCCAGC

CGTTTATTTGGTGTATGCTTCACAATTTTGGCGGAAATCATGGGCTGTTCGGTGCCCTGGAGGCCGT

CAATGGGGGACCTGAGGCTGCAAGATTGTTCCCAAACTCAACCATGGTGGGGACCGGAATGGCAC

CCGAAGGCATTAGCCAGAATGAGGTCGTCTACAGTCTGATGGCGGAATTGGGGTGGCGGAAGGAC

CCCGTGCCAGATCTCGCCGCCTGGGTGACTAGCTTTGCCGCCCGCCGCTATGGAGTGAGCCATCCT

GATGCAGGCGCAGCCTGGCGGCTGTTGCTTCGATCAGTATACAATTGTTCAGGAGAGGCCTGCCGG

GGGCACAATAGGAGCCCACTGGTAAGGAGGCCCAGCCTGCAGATGAACACCTCTATCTGGTACAA

CAGAAGCGATGTTTTCGAGGCTTGGAGACTTCTCCTTACATCTGCCCCTAGCTTGGCCACCAGTCC

AGCCTTCCGATATGATCTGCTGGACCTCACCCGACAGGCCGTGCAGGAACTGGTCTCTCTCTACTA

TGAAGAGGCCAGATCAGCTTACCTCTCTAAAGAACTGGCCTCCCTCTTGCGAGCAGGAGGCGTCCT

GGCATATGAGCTGCTCCCTGCACTGGACGAGGTACTGGCATCTGATTCCCGATTCCTGCTCGGGTC

ATGGCTGGAGCAAGCCCGAGCAGCGGCTGTAAGCGAGGCTGAAGCAGACTTCTATGAACAAAATA

GTAGGTATCAACTGACTCTGTGGGGTCCAGAGGGGAATATCCTGGACTACGCGAACAAACAGTTG

GCGGGCCTGGTGGCCAACTACTACACCCCTCGGTGGAGATTGTTTTTGGAGGCGCTGGTGGATTCA

GTCGCACAGGGGATTCCGTTTCAGCAACATCAGTTTGACAAGAACGTCTTTCAGCTGGAACAGGCT

TTTGTGCTTTCTAAGCAGCGCTACCCTTCTCAGCCAAGAGGCGATACCGTTGACCTCGCGAAGAAA

ATCTTTCTCAAGTACTATCCCAGATGGGTGGCCGGATCATGGTAGgtcgacccTCGACTAGAGCTCGCT

GATCAGCCTCGACTGTGCCTTCTAGTTGCCAGCCATCTGTTGTTTGCCCCTCCCCCGTGCCTTCCTT

GACCCTGGAAGGTGCCACTCCCACTGTCCTTTCCTAATAAAATGAGGAAATTGCATCGCATTGTCT

GAGTAGGTGTCATTCTATTCTGGGGGGTGGGGTGGGGCAGGACAGCAAGGGGGAGGATTGGGAA

GACAATAGCAGGCATGCTGGGGAGAGATCTAGGAACCCCTAGTGATGGAGTTGGCCACTCCCTCT

CTGCGCGCTCGCTCGCTCACTGAGGCCGCCCGGGCAAAGCCCGGGCGTCGGGCGACCTTTGGTCGC

CCGGCCTCAGTGAGCGAGCGAGCGCGCAGAGAGGGAGTGGCCAACCCCCCCCCCCCCCCCCCCCTGC

AGCCAGCTGGCGTAATAGCGAAGAGGCCCGCACCGATCGCCCTTCCCAACAGTTGCGTAGCCTGA

ATGGCGAATGGCGCGACGCGCCCTGTAGCGGCGCATTAAGCGCGGCGGGTGTGGTGGTTACGCGC

AGCGTGACCGCTACACTTGCCAGCGCCCTAGCGCCCGCTCCTTTCGCTTTCTTCCCTTCCTTTCTCG

CCACGTTCGCCGGCTTTCCCCGTCAAGCTCTAAATCGGGGGCTCCCTTTAGGGTTCCGATTTAGTGC

TTTACGGCACCTCGACCCCAAAAAACTTGATTAGGGTGATGGTTCACGTAGTGGGCCATCGCCCTG

ATAGACGGTTTTTCGCCCTTTGACGTTGGAGTCCACGTTCTTTAATAGTGGACTCTTGTTCCAAACT

GGAACAACACTCAACCCTATCTCGGTCTATTCTTTTGATTTATAAGGGATTTTGCCGATTTCGGCCT

ATTGGTTAAAAAATGAGCTGATTTAACAAAAATTTAACGCGAATTTTAACAAAATATTAACGTTTA

CAATTTCCTGATGCGGTATTTTCTCCTTACGCATCTGTGCGGTATTTCACACCGCATATGGTGCACT

CTCAGTACAATCTGCTCTGATGCCGCATAGTTAAGCCAGCCCCGACACCCGCCAACACCCGCTGAC

GCGCCCTGACGGGCTTGTCTGCTCCCGGCATCCGCTTACAGACAAGCTGTGACCGTCTCCGGGAGC

TGCATGTGTCAGAGGTTTTCACCGTCATCACCGAAACGCGCGAGACGAAAGGGCCTCGTGATACG

CCTATTTTTATAGGTTAATGTCATGATAATAATGGTTTCTTAGACGTCAGGTGGCACTTTTCGGGGA

AATGTGCGCGGAACCCCTATTTGTTTATTTTTCTAAATACATTCAAATATGTATCCGCTCATGAGAC

AATAACCCTGATAAATGCTTCAATAATATTGAAAAAGGAAGAGTATGAGTATTCAACATTTCCGTG
```

TCGCCCTTATTCCCTTTTTTGCGGCATTTTGCCTTCCTGTTTTTGCTCACCCAGAAACGCTGGTGAAA

GTAAAAGATGCTGAAGATCAGTTGGGTGCACGAGTGGGTTACATCGAACTGGATCTCAACAGCGG

TAAGATCCTTGAGAGTTTTCGCCCCGAAGAACGTTTTCCAATGATGAGCACTTTTAAAGTTCTGCT

ATGTGGCGCGGTATTATCCCGTATTGACGCCGGGCAAGAGCAACTCGGTCGCCGCATACACTATTC

TCAGAATGACTTGGTTGAGTACTCACCAGTCACAGAAAAGCATCTTACGGATGGCATGACAGTAA

GAGAATTATGCAGTGCTGCCATAACCATGAGTGATAACACTGCGGCCAACTTACTTCTGACAACGA

TCGGAGGACCGAAGGAGCTAACCGCTTTTTTGCACAACATGGGGGATCATGTAACTCGCCTTGATC

GTTGGGAACCGGAGCTGAATGAAGCCATACCCAAACGACGAGCGTGACACCACGATGCCTGTAGCA

ATGGCAACAACGTTGCGCAAACTATTAACTGGCGAACTACTTACTCTAGCTTCCCGGCAACAATTA

ATAGACTGGATGGAGGCGGATAAAGTTGCAGGACCACTTCTGCGCTCGGCCCTTCCGGCTGGCTG

GTTTATTGCTGATAAATCTGGAGCCGGTGAGCGTGGGTCTCGCGGTATCATTGCAGCACTGGGGCC

AGATGGTAAGCCCTCCCGTATCGTAGTTATCTACACGACGGGGAGTCAGGCAACTATGACCTTCCA

GGGTCAAGGAAGCTGTCAGACCAAGTTTACTCATATATACTTTAGATTGATTTAAAACTTCATTTTT

AATTTAAAAGGATCTAGGTGAAGATCCTTTTTGATAATCTCATGACCAAAATCCCTTAACGTGAGT

TTTCGTTCCACTGAGCGTCAGACCCCGTAGAAAAGATCAAAGGATCTTCTTGAGATCCTTTTTTTCT

GCGCGTAATCTGCTGCTTGCAAACAAAAAAACCACCGCTACCAGCGGTGGTTTGTTTGCCGGATCA

AGAGCTACCAACTCTTTTTCCGAAGGTAACTGGCTTCAGCAGAGCGCAGATACCAAATACTGTCCT

TCTAGTGTAGCCGTAGTTAGGCCACCACTTCAAGAACTCTGTAGCACCGCCTACATACCTCGCTCT

GCTAATCCTGTTACCAGTGGCTGCTGCCAGTGGCGATAAGTCGTGTCTTACCGGGTTGGACTCAAG

ACGATAGTTACCGGATAAGGCGCAGCGGTCGGGCTGAACGGGGGGTTCGTGCACACAGCCCAGCT

TGGAGCGAACGACCTACACCGAACTGAGATACCTACAGCGTGAGCATTGAGAAAGCGCCACGCTT

CCCGAAGGGAGAAAGGCGGACAGGTATCCGGTAAGCGGCAGGGTCGGAACAGGAGAGCGCACGA

GGGAGCTTCCAGGGGGAAACGCCTGGTATCTTTATAGTCCTGTCGGGTTTCGCCACCTCTGACTTG

AGCGTCGATTTTTGTGATGCTCGTCAGGGGGGCGGAGCCTATGGAAAAACGCCAGCAACGCGGCC

TTTTTACGGTTCCTGGCCTTTTGCTGGCCTTTTGCTCACATGTTCTTTCCTGCGTTATCCCCTGATTC

TGTGGATAACCGTATTACCGCCTTTGAGTGAGCTGATACCGCTCGCCGCAGCCGAACGACCGAGCG

CAGCGAGTCAGTGAGCGAGGAAGCGGAAGAGCGCCCAATACGCAAACCGCCTCTCCCCGCGCGTT

GGCCGATTCATTAATGCAGCTGGGCTGCA pTR-CMV-NAGLU-op

SEQ ID NO: 4

GGGGGGGGGGGGGGGGGGTTGGCCACTCCCTCTCTGCGCGCTCGCTCGCTCACTGAGGCCGGGCG

ACCAAAGGTCGCCCGACGCCCGGGCTTTGCCCGGGCGGCCTCAGTGAGCGAGCGAGCGCGCAGAG

AGGGAGTGGCCAACTCCATCACTAGGGGTTCCTAGATCTGAATTCGGTACCCGTTACATAACTTAC

GGTAAATGGCCCGCCTGGCTGACCGCCCAACGACCCCCGCCCATTGACGTCAATAATGACGTATGT

TCCCATAGTAACGCCAATAGGGACTTTCCATTGACGTCAATGGGTGGAGTATTTACGGTAAACTGC

CCACTTGGCAGTACATCAAGTGTATCATATGCCAAGTACGCCCCCTATTGACGTCAATGACGGTAA

ATGGCCCGCCTGGCATTATGCCCAGTACATGACCTTATGGGACTTTCCTACTTGGCAGTACATCTA

CGTATTAGTCATCGCTATTACCATGGTGATGCGGTTTTGGCAGTACATCAATGGGCGTGGATAGCG

GTTTGACTCACGGGGATTTCCAAGTCTCCACCCCATTGACGTCAATGGGAGTTTGTTTTGGCACCA

AAATCAACGGGACTTTCCAAAATGTCGTAACAACTCCGCCCCATTGACGCAAATGGGCGGTAGGC

GTGTACGGTGGGAGGTCTATATAAGCAGAGCTCGTTTAGTGAACCGTCAGATCGCCTGGAGACGC

-continued

```
CATCCACGCTGTTTTGACCTCCATAGAAGACACCGGGACCGATCCAGCCTCCGGACTCTAGAGGAT

CCGGTACTCGAGGAACTGAAAAACCAGAAAGTTAACTGGTAAGTTTAGTCTTTTTGTCTTTTATTTC

AGGTCCCGGATCCGGTGGTGGTGCAAATCAAAGAACTGCTCCTCAGTGGATGTTGCCTTTACTTCT

AGGCCTGTACGGAAGTGTTACTTCTGCTCTAAAAGCTGCGGAATTGTACCCGCGGCCCGGGATCCA

CCGGCCACCGGtATTCgcAGACCATGGAGGCTGTTGCTGTTGCAGCCGCTGTGGGCGTCTTGCTGTT

GGCCGGTGCCGGGGGAGCTGCTGGCGACGAGGCAAGGGAAGCTGCAGCTGTGCGGGCTCTCGTCG

CAAGGTTGCTGGGTCCAGGTCCCGCTGCTGACTTTAGTGTGTCAGTGGAGAGGGCTTTGGCCGCTA

AACCTGGCCTGGACACCTACTCCCTGGGTGGAGGTGGGGCTGCCCGCGTGAGGGTGAGAGGCTCA

ACGGGGGTGGCTGCTGCAGCAGGTCTGCATAGGTACCTCAGAGACTTCTGCGGATGCCATGTCGCT

TGGAGCGGCAGTCAACTGAGGCTGCCCCGGCCCCTCCCTGCCGTCCCTGGGGAACTTACAGAAGCT

ACTCCAAATAGGTACAGATATTATCAAAATGTGTGTACGCAGAGTTACAGCTTTGTGTGGTGGGAC

TGGGCAAGGTGGGAGCGCGAAATCGATTGGATGGCCCTCAACGGGATCAATCTGGCCTTGGCATG

GTCCGGACAGGAAGCTATCTGGCAGCGCGTGTATCTGGCTCTCGGGTTGACTCAAGCTGAAATCAA

CGAGTTTTTCACAGGCCCCGCCTTCCTGGCCTGGGGGCGGATGGGTAATCTTCATACTTGGGACGG

GCCACTGCCCCCCTCTTGGCACATCAAACAGTTGTATCTGCAGCACCGCGTCCTGGACCAGATGCG

CAGCTTCGGCATGACTCCCGTCCTGCCGGCTTTCGCAGGGCACGTCCCAGAGGCGGTCACACGGGT

CTTCCCTCAGGTGAATGTGACAAAAATGGGATCATGGGGACATTTCAATTGTTCTTACAGTTGTTC

CTTCCTGCTGGCACCCGAAGATCCTATCTTCCCAATCATAGGAAGTCTCTTTCTGCGCGAGTTGATT

AAGGAGTTCGGTACTGATCACATTTATGGCGCTGATACTTTTAACGAAATGCAGCCCCCCTCTTCT

GAACCATCCTATCTTGCTGCCGCAACCACTGCCGTTTATGAAGCCATGACCGCCGTGGACACTGAA

GCCGTTTGGCTTCTCCAAGGTTGGCTGTTCCAGCACCAGCCTCAGTTTTGGGGGCCAGCTCAGATA

AGAGCCGTTCTCGGCGCTGTACCTCGCGGAAGACTGCTGGTGCTTGATTTGTTCGCAGAGTCTCAG

CCAGTGTACACGAGAACCGCTTCCTTCCAGGGCCAGCCGTTTATTTGGTGTATGCTTCACAATTTTG

GCGGAAATCATGGGCTGTTCGGTGCCCTGGAGGCCGTCAATGGGGGACCTGAGGCTGCAAGATTG

TTCCCAAACTCAACCATGGTGGGGACCGGAATGGCACCCGAAGGCATTAGCCAGAATGAGGTCGT

CTACAGTCTGATGGCGGAATTGGGGTGGCGGAAGGACCCCGTGCCAGATCTCGCCGCCTGGGTGA

CTAGCTTTGCCGCCCGCCGCTATGGAGTGAGCCATCCTGATGCAGGCGCAGCCTGGCGGCTGTTGC

TTCGATCAGTATACAATTGTTCAGGAGAGGCCTGCCGGGGGCACAATAGGAGCCCACTGGTAAGG

AGGCCCAGCCTGCAGATGAACACCTCTATCTGGTACAACAGAAGCGATGTTTTCGAGGCTTGGAG

ACTTCTCCTTACATCTGCCCCTAGCTTGGCCACCAGTCCAGCCTTCCGATATGATCTGCTGGACCTC

ACCCGACAGGCCGTGCAGGAACTGGTCTCTCTCTACTATGAAGAGGCCAGATCAGCTTACCTCTCT

AAAGAACTGGCCTCCCTCTTGCGAGCAGGAGGCGTCCTGGCATATGAGCTGCTCCCTGCACTGGAC

GAGGTACTGGCATCTGATTCCCGATTCCTGCTCGGGTCATGGCTGGAGCAAGCCCGAGCAGCGGCT

GTAAGCGAGGCTGAAGCAGACTTCTATGAACAAAATAGTAGGTATCAACTGACTCTGTGGGGTCC

AGAGGGGAATATCCTGGACTACGCGAACAAACAGTTGGCGGGCCTGGTGGCCAACTACTACACCC

CTCGGTGGAGATTGTTTTTGGAGGCGCTGGTGGATTCAGTCGCACAGGGGATTCCGTTTCAGCAAC

ATCAGTTTGACAAGAACGTCTTTCAGCTGGAACAGGCTTTTGTGCTTTCTAAGCAGCGCTACCCTTC

TCAGCCAAGAGGCGATACCGTTGACCTCGCGAAGAAAATCTTTCTCAAGTACTATCCCAGATGGGT

GGCCGGATCATGGTAGgtcgacccTCGACTAGAGCTCGCTGATCAGCCTCGACTGTGCCTTCTAGTTGC

CAGCCATCTGTTGTTTGCCCCTCCCCCGTGCCTTCCTTGACCCTGGAAGGTGCCACTCCCACTGTCC

TTTCCTAATAAAATGAGGAAATTGCATCGCATTGTCTGAGTAGGTGTCATTCTATTCTGGGGGGTG
```

GGGTGGGGCAGGACAGCAAGGGGGAGGATTGGGAAGACAATAGCAGGCATGCTGGGGAGAGATC

TAGGAACCCCTAGTGATGGAGTTGGCCACTCCCTCTCTGCGCGCTCGCTCGCTCACTGAGGCCGCC

CGGGCAAAGCCCGGGCGTCGGGCGACCTTTGGTCGCCCGGCCTCAGTGAGCGAGCGAGCGCGCAG

AGAGGGAGTGGCCAACCCCCCCCCCCCCCCCCCCTGCAGCCAGCTGGCGTAATAGCGAAGAGGCCC

GCACCGATCGCCCTTCCCAACAGTTGCGTAGCCTGAATGGCGAATGGCGCGACGCGCCCTGTAGC

GGCGCATTAAGCGCGGCGGGTGTGGTGGTTACGCGCAGCGTGACCGCTACACTTGCCAGCGCCCT

AGCGCCCGCTCCTTTCGCTTTCTTCCCTTCCTTTCTCGCCACGTTCGCCGGCTTTCCCCGTCAAGCTC

TAAATCGGGGGCTCCCTTTAGGGTTCCGATTTAGTGCTTTACGGCACCTCGACCCCAAAAAACTTG

ATTAGGGTGATGGTTCACGTAGTGGGCCATCGCCCTGATAGACGGTTTTTCGCCCTTTGACGTTGG

AGTCCACGTTCTTTAATAGTGGACTCTTGTTCCAAACTGGAACAACACTCAACCCTATCTCGGTCTA

TtctTTTGATTTATAAGGGATTTTGCCGATTTCGGCCTATTGGTTAAAAAATGAGCTGATTTAACAA

AAATTTAACGCGAATTTTAACAAAATATTAACGTTTACAATTTCCTGATGCGGTATTTTCTCCTTAC

GCATCTGTGCGGTATTTCACACCGCATATGGTGCACTCTCAGTACAATCTGCTCTGATGCCGCATA

GTTAAGCCAGCCCCGACACCCGCCAACACCCGCTGACGCGCCCTGACGGGCTTGTCTGCTCCCGGC

ATCCGCTTACAGACAAGCTGTGACCGTCTCCGGGAGCTGCATGTGTCAGAGGTTTTCACCGTCATC

ACCGAAACGCGCGAGACGAAAGGGCCTCGTGATACGCCTATTTTTATAGGTTAATGTCATGATAAT

AATGGTTTCTTAGACGTCAGGTGGCACTTTTCGGGGAAATGTGCGCGGAACCCCTATTTGTTTATTT

TTCTAAATACATTCAAATATGTATCCGCTCATGAGACAATAACCCTGATAAATGCTTCAATAATAT

TGAAAAAGGAAGAGTATGAGTATTCAACATTTCCGTGTCGCCCTTATTCCCTTTTTTGCGGCATTTT

GCCTTCCTGTTTTTGCTCACCCAGAAACGCTGGTGAAAGTAAAAGATGCTGAAGATCAGTTGGGTG

CACGAGTGGGTTACATCGAACTGGATCTCAACAGCGGTAAGATCCTTGAGAGTTTTCGCCCCGAAG

AACGTTTTCCAATGATGAGCACTTTTAAAGTTCTGCTATGTGGCGCGGTATTATCCCGTATTGACGC

CGGGCAAGAGCAACTCGGTCGCCGCATACACTATTCTCAGAATGACTTGGTTGAGTACTCACCAGT

CACAGAAAAGCATCTTACGGATGGCATGACAGTAAGAGAATTATGCAGTGCTGCCATAACCATGA

GTGATAACACTGCGGCCAACTTACTTCTGACAACGATCGGAGGACCGAAGGAGCTAACCGCTTTTT

TGCACAACATGGGGGATCATGTAACTCGCCTTGATCGTTGGGAACCGGAGCTGAATGAAGCCATA

CCAAACGACGAGCGTGACACCACGATGCCTGTAGCAATGGCAACAACGTTGCGCAAACTATTAAC

TGGCGAACTACTTACTCTAGCTTCCCGGCAACAATTAATAGACTGGATGGAGGCGGATAAAGTTGC

AGGACCACTTCTGCGCTCGGCCCTTCCGGCTGGCTGGTTTATTGCTGATAAATCTGGAGCCGGTGA

GCGTGGGTCTCGCGGTATCATTGCAGCACTGGGGCCAGATGGTAAGCCCTCCCGTATCGTAGTTAT

CTACACGACGGGGAGTCAGGCAACTATGACCTTCCAGGGTCAAGGAAGCTGTCAGACCAAGTTTA

CTCATATATACTTTAGATTGATTTAAAACTTCATTTTTAATTTAAAAGGATCTAGGTGAAGATCCTT

TTTGATAATCTCATGACCAAAATCCCTTAACGTGAGTTTTCGTTCCACTGAGCGTCAGACCCCGTA

GAAAAGATCAAAGGATCTTCTTGAGATCCTTTTTTTCTGCGCGTAATCTGCTGCTTGCAAACAAAA

AAACCACCGCTACCAGCGGTGGTTTGTTTGCCGGATCAAGAGCTACCAACTCTTTTTTCCGAAGGTA

ACTGGCTTCAGCAGAGCGCAGATACCAAATACTGTCCTTCTAGTGTAGCCGTAGTTAGGCCACCAC

TTCAAGAACTCTGTAGCACCGCCTACATACCTCGCTCTGCTAATCCTGTTACCAGTGGCTGCTGCCA

GTGGCGATAAGTCGTGTCTTACCGGGTTGGACTCAAGACGATAGTTACCGGATAAGGCGCAGCGG

TCGGGCTGAACGGGGGGTTCGTGCACACAGCCCAGCTTGGAGCGAACGACCTACACCGAACTGAG

ATACCTACAGCGTGAGCATTGAGAAAGCGCCACGCTTCCCGAAGGGAGAAAGGCGGACAGGTATC

-continued

```
CGGTAAGCGGCAGGGTCGGAACAGGAGAGCGCACGAGGGAGCTTCCAGGGGGAAACGCCTGGTA

TCTTTATAGTCCTGTCGGGTTTCGCCACCTCTGACTTGAGCGTCGATTTTTGTGATGCTCGTCAGGG

GGGCGGAGCCTATGGAAAAACGCCAGCAACGCGGCCTTTTTACGGTTCCTGGCCTTTTGCTGGCCT

TTTGCTCACATGTTCTTTCCTGCGTTATCCCCTGATTCTGTGGATAACCGTATTACCGCCTTTGAGTG

AGCTGATACCGCTCGCCGCAGCCGAACGACCGAGCGCAGCGAGTCAGTGAGCGAGGAAGCGGAA

GAGCGCCCAATACGCAAACCGCCTCTCCCCGCGCGTTGGCCGATTCATTAATGCAGCTGGGCTGCA
```

Methods of Producing Virus Vectors

The present invention further provides methods of producing virus vectors. In one particular embodiment, the present invention provides a method of producing a recombinant parvovirus particle, comprising providing to a cell permissive for parvovirus replication: (a) a recombinant parvovirus template comprising (i) the nucleic acid encoding NAGLU of the invention, and (ii) a parvovirus ITR; (b) a polynucleotide comprising Rep and Cap coding sequences; under conditions sufficient for the replication and packaging of the recombinant parvovirus template; whereby recombinant parvovirus particles are produced in the cell. Conditions sufficient for the replication and packaging of the recombinant parvovirus template can be, e.g., the presence of AAV sequences sufficient for replication of the parvovirus template and encapsidation into parvovirus capsids (e.g., parvovirus rep sequences and parvovirus cap sequences) and helper sequences from adenovirus and/or herpesvirus. In particular embodiments, the parvovirus template comprises two parvovirus ITR sequences, which are located 5' and 3' to the heterologous nucleic acid sequence, although they need not be directly contiguous thereto.

In some embodiments, the recombinant parvovirus template comprises an ITR that is not resolved by Rep to make duplexed AAV vectors as described in international patent publication WO 01/92551.

The parvovirus template and parvovirus rep and cap sequences are provided under conditions such that virus vector comprising the parvovirus template packaged within the parvovirus capsid is produced in the cell. The method can further comprise the step of collecting the virus vector from the cell. The virus vector can be collected from the medium and/or by lysing the cells.

The cell can be a cell that is permissive for parvoviral viral replication. Any suitable cell known in the art may be employed. In particular embodiments, the cell is a mammalian cell (e.g., a primate or human cell). As another option, the cell can be a trans-complementing packaging cell line that provide functions deleted from a replication-defective helper virus, e.g., 293 cells or other E1a trans-complementing cells.

The parvovirus replication and capsid sequences may be provided by any method known in the art. Current protocols typically express the parvovirus rep/cap genes on a single plasmid. The parvovirus replication and packaging sequences need not be provided together, although it may be convenient to do so. The parvovirus rep and/or cap sequences may be provided by any viral or non-viral vector. For example, the rep/cap sequences may be provided by a hybrid adenovirus or herpesvirus vector (e.g., inserted into the E1a or E3 regions of a deleted adenovirus vector). EBV vectors may also be employed to express the parvovirus cap and rep genes. One advantage of this method is that EBV vectors are episomal, yet will maintain a high copy number throughout successive cell divisions (i.e., are stably integrated into the cell as extra-chromosomal elements, designated as an "EBV based nuclear episome," see Margolski, (1992) *Curr. Top. Microbiol. Immun.* 158:67).

As a further alternative, the rep/cap sequences may be stably incorporated into a cell.

Typically the parvovirus rep/cap sequences will not be flanked by the TRs, to prevent rescue and/or packaging of these sequences.

The parvovirus template can be provided to the cell using any method known in the art. For example, the template can be supplied by a non-viral (e.g., plasmid) or viral vector. In particular embodiments, the parvovirus template is supplied by a herpesvirus or adenovirus vector (e.g., inserted into the E1a or E3 regions of a deleted adenovirus). As another illustration, Palombo et al., (1998) *J. Virology* 72:5025, describes a baculovirus vector carrying a reporter gene flanked by the AAV TRs. EBV vectors may also be employed to deliver the template, as described above with respect to the rep/cap genes.

In another representative embodiment, the parvovirus template is provided by a replicating rAAV virus. In still other embodiments, an AAV provirus comprising the parvovirus template is stably integrated into the chromosome of the cell.

To enhance virus titers, helper virus functions (e.g., adenovirus or herpesvirus) that promote a productive parvovirus infection can be provided to the cell. Helper virus sequences necessary for parvovirus replication are known in the art. Typically, these sequences will be provided by a helper adenovirus or herpesvirus vector. Alternatively, the adenovirus or herpesvirus sequences can be provided by another non-viral or viral vector, e.g., as a non-infectious adenovirus miniplasmid that carries all of the helper genes that promote efficient parvovirus production as described by Ferrari et al., (1997) *Nature Med.* 3:1295, and U.S. Pat. Nos. 6,040,183 and 6,093,570.

Further, the helper virus functions may be provided by a packaging cell with the helper sequences embedded in the chromosome or maintained as a stable extrachromosomal element. Generally, the helper virus sequences cannot be packaged into AAV virions, e.g., are not flanked by ITRs.

Those skilled in the art will appreciate that it may be advantageous to provide the parvovirus replication and capsid sequences and the helper virus sequences (e.g., adenovirus sequences) on a single helper construct. This helper construct may be a non-viral or viral construct. As one nonlimiting illustration, the helper construct can be a hybrid adenovirus or hybrid herpesvirus comprising the AAV rep/cap genes.

In one particular embodiment, the parvovirus rep/cap sequences and the adenovirus helper sequences are supplied by a single adenovirus helper vector. This vector can further comprise the parvovirus template. The parvovirus rep/cap sequences and/or the parvovirus template can be inserted into a deleted region (e.g., the E1a or E3 regions) of the adenovirus.

In a further embodiment, the parvovirus rep/cap sequences and the adenovirus helper sequences are supplied by a single adenovirus helper vector. According to this embodiment, the parvovirus template can be provided as a plasmid template.

In another illustrative embodiment, the parvovirus rep/cap sequences and adenovirus helper sequences are provided by a single adenovirus helper vector, and the parvovirus template is integrated into the cell as a provirus. Alternatively, the parvovirus template is provided by an EBV vector that is maintained within the cell as an extrachromosomal element (e.g., as an EBV based nuclear episome).

In a further exemplary embodiment, the parvovirus rep/cap sequences and adenovirus helper sequences are provided by a single adenovirus helper. The parvovirus template can be provided as a separate replicating viral vector. For example, the parvovirus template can be provided by a parvovirus particle or a second recombinant adenovirus particle.

According to the foregoing methods, the hybrid adenovirus vector typically comprises the adenovirus 5' and 3' cis sequences sufficient for adenovirus replication and packaging (i.e., the adenovirus terminal repeats and PAC sequence). The parvovirus rep/cap sequences and, if present, the AAV template are embedded in the adenovirus backbone and are flanked by the 5' and 3' cis sequences, so that these sequences may be packaged into adenovirus capsids. As described above, the adenovirus helper sequences and the parvovirus rep/cap sequences are generally not flanked by ITRs so that these sequences are not packaged into the parvovirus virions.

Zhang et al., ((2001) *Gene Ther.* 18:704-12) describe a chimeric helper comprising both adenovirus and the AAV rep and cap genes.

Herpesvirus may also be used as a helper virus in parvovirus packaging methods. Hybrid herpesviruses encoding the parvovirus Rep protein(s) may advantageously facilitate scalable parvovirus vector production schemes. A hybrid herpes simplex virus type I (HSV-1) vector expressing the AAV-2 rep and cap genes has been described (Conway et al., (1999) *Gene Ther.* 6:986 and WO 00/17377.

As a further alternative, the virus vectors of the invention can be produced in insect cells using baculovirus vectors to deliver the rep/cap genes and parvovirus template as described, for example, by Urabe et al., (2002) *Human Gene Ther.* 13:1935-43.

Parvovirus vector stocks free of contaminating helper virus may be obtained by any method known in the art. For example, parvovirus and helper virus may be readily differentiated based on size. Parvovirus may also be separated away from helper virus based on affinity for a heparin substrate (Zolotukhin et al., (1999) *Gene Therapy* 6:973). Deleted replication-defective helper viruses can be used so that any contaminating helper virus is not replication competent. As a further alternative, an adenovirus helper lacking late gene expression may be employed, as only adenovirus early gene expression is required to mediate packaging of parvovirus. Adenovirus mutants defective for late gene expression are known in the art (e.g., ts100K and ts149 adenovirus mutants).

Recombinant Virus Vectors

The virus vectors of the present invention are useful for the delivery of nucleic acids to cells in vitro, ex vivo, and in vivo. In particular, the virus vectors can be advantageously employed to deliver or transfer nucleic acids to animal, including mammalian, cells. In particular, the virus vectors of the present invention are useful for the delivery of a nucleic acid encoding NAGLU to a subject.

It will be understood by those skilled in the art that the nucleic acid encoding NAGLU can be operably associated with appropriate control sequences. For example, the nucleic acid can be operably associated with expression control elements, such as transcription/translation control signals, origins of replication, polyadenylation signals, internal ribosome entry sites (IRES), promoters, and/or enhancers, and the like.

Those skilled in the art will appreciate that a variety of promoter/enhancer elements can be used depending on the level and tissue-specific expression desired. The promoter/enhancer can be constitutive or inducible, depending on the pattern of expression desired. The promoter/enhancer can be native or foreign and can be a natural or a synthetic sequence. By foreign, it is intended that the transcriptional initiation region is not found in the wild-type host into which the transcriptional initiation region is introduced.

In particular embodiments, the promoter/enhancer elements can be native to the target cell or subject to be treated. In representative embodiments, the promoters/enhancer element can be native to the NAGLU nucleic acid sequence. The promoter/enhancer element is generally chosen so that it functions in the target cell(s) of interest. Further, in particular embodiments the promoter/enhancer element is a mammalian promoter/enhancer element. In particular embodiments, the promoter/enhancer element functions in all cells so that NAGLU is expressed systemically. The promoter/enhancer element may be constitutive or inducible.

Inducible expression control elements are typically advantageous in those applications in which it is desirable to provide regulation over expression of the nucleic acid sequence. Inducible promoters/enhancer elements for gene delivery can be tissue-specific or -preferred promoter/enhancer elements, and include neuron specific or preferred promoter/enhancer elements. Other inducible promoter/enhancer elements include hormone-inducible and metal-inducible elements. Exemplary inducible promoters/enhancer elements include, but are not limited to, a Tet on/off element, a RU486-inducible promoter, an ecdysone-inducible promoter, a rapamycin-inducible promoter, and a metallothionein promoter.

In embodiments wherein the nucleic acid sequence is transcribed and then translated in the target cells, specific initiation signals are generally included for efficient translation of inserted protein coding sequences. These exogenous translational control sequences, which may include the ATG initiation codon and adjacent sequences, can be of a variety of origins, both natural and synthetic.

The virus vectors of the invention can be parvovirus vectors, e.g., AAV vectors. The AAV vectors may be any AAV serotype. In some embodiments, the AAV vector is an AAV2, AAV8, or AAV9 vector. In some embodiments, the AAV vector is a hybrid vector, e.g., one having a capsid protein from one serotype and a genome from another serotype or one having a synthetic capsid protein. In certain embodiments, the vector comprises a hybrid capsid with an altered tropism. In one example the hybrid capsid comprising a glycan binding site (e.g., a galactose binding site) from one serotype (e.g., AAV9) in a capsid sequence from another serotype (e.g., AAV8) (see, e.g., WO 2014/144229, incorporated by reference herein in its entirety).

The virus vectors according to the present invention provide a means for delivering NAGLU nucleic acids into a broad range of cells, including dividing and non-dividing cells. The virus vectors can be employed to deliver the nucleic acid to a cell in vitro, e.g., to produce a polypeptide in vitro or for ex vivo gene therapy. The virus vectors are additionally useful in a method of delivering the nucleic acid to a subject in need thereof, e.g., to express NAGLU. In this manner, the polypeptide can be produced in vivo in the subject. The subject can be in need of the polypeptide because the subject has a deficiency of the polypeptide. Further, the method can be practiced because the production of the polypeptide in the subject may impart some beneficial effect.

The virus vectors can also be used to produce NAGLU in cultured cells or in a subject (e.g., using the subject as a bioreactor to produce the polypeptide or to observe the effects of the polypeptide on the subject, for example, in connection with screening methods).

The virus vectors of the present invention can be employed to deliver a nucleic acid encoding NAGLU to treat and/or prevent any disease state for which it is beneficial to deliver NAGLU, e.g., MPS IIIB.

Virus vectors according to the instant invention find use in diagnostic and screening methods, whereby the NAGLU nucleic acid is transiently or stably expressed in a cell culture system, in an organ or organ culture, or alternatively, a transgenic animal model.

The virus vectors of the present invention can also be used for various non-therapeutic purposes, including but not limited to use in protocols to assess gene targeting, clearance, transcription, translation, etc., as would be apparent to one skilled in the art. The virus vectors can also be used for the purpose of evaluating safety (spread, toxicity, immunogenicity, etc.). Such data, for example, are considered by the United States Food and Drug Administration as part of the regulatory approval process prior to evaluation of clinical efficacy.

Alternatively, the virus vector may be administered to a cell ex vivo, and the altered cell is administered to the subject. The virus vector comprising the NAGLU nucleic acid is introduced into the cell, and the cell is administered to the subject, where the nucleic acid can be expressed.

Subjects, Pharmaceutical Formulations, and Modes of Administration

Virus vectors and capsids according to the present invention find use in both veterinary and medical applications. Suitable subjects include both avians and mammals. The term "avian" as used herein includes, but is not limited to, chickens, ducks, geese, quail, turkeys, pheasant, parrots, parakeets, and the like. The term "mammal" as used herein includes, but is not limited to, humans, non-human primates, bovines, ovines, caprines, equines, felines, canines, lagomorphs, etc. Human subjects include neonates, infants, juveniles and adults.

In particular embodiments, the present invention provides a pharmaceutical composition comprising a virus vector of the invention in a pharmaceutically acceptable carrier and, optionally, other medicinal agents, pharmaceutical agents, stabilizing agents, buffers, carriers, adjuvants, diluents, etc. For injection, the carrier will typically be a liquid. For other methods of administration, the carrier may be either solid or liquid. For inhalation administration, the carrier will be respirable, and optionally can be in solid or liquid particulate form.

By "pharmaceutically acceptable" it is meant a material that is not toxic or otherwise undesirable, i.e., the material may be administered to a subject without causing any undesirable biological effects.

One aspect of the present invention is a method of transferring a nucleic acid to a cell in vitro. The virus vector may be introduced into the cells at the appropriate multiplicity of infection according to standard transduction methods suitable for the particular target cells. Titers of virus vector to administer can vary, depending upon the target cell type and number, and the particular virus vector, and can be determined by those of skill in the art without undue experimentation. In representative embodiments, at least about $10^3$ infectious units, more preferably at least about $10^5$ infectious units are introduced to the cell.

The cell(s) into which the virus vector is introduced can be of any type. Moreover, the cell can be from any species of origin, as indicated above.

The virus vector can be introduced into cells in vitro for the purpose of administering the modified cell to a subject. In particular embodiments, the cells have been removed from a subject, the virus vector is introduced therein, and the cells are then administered back into the subject. Methods of removing cells from subject for manipulation ex vivo, followed by introduction back into the subject are known in the art (see, e.g., U.S. Pat. No. 5,399,346). Alternatively, the recombinant virus vector can be introduced into cells from a donor subject, into cultured cells, or into cells from any other suitable source, and the cells are administered to a subject in need thereof (i.e., a "recipient" subject).

Suitable cells for ex vivo gene delivery are as described above. Dosages of the cells to administer to a subject will vary upon the age, condition and species of the subject, the type of cell, the nucleic acid being expressed by the cell, the mode of administration, and the like. Typically, at least about $10^2$ to about $10^8$ cells or at least about $10^3$ to about $10^6$ cells will be administered per dose in a pharmaceutically acceptable carrier. In particular embodiments, the cells transduced with the virus vector are administered to the subject in a treatment effective or prevention effective amount in combination with a pharmaceutical carrier.

A further aspect of the invention is a method of administering the virus vector to subjects. Administration of the virus vectors according to the present invention to a human subject or an animal in need thereof can be by any means known in the art. Optionally, the virus vector is delivered in a treatment effective or prevention effective dose in a pharmaceutically acceptable carrier.

Dosages of the virus vector to be administered to a subject depend upon the mode of administration, the disease or condition to be treated and/or prevented, the individual subject's condition, the particular virus vector, and the nucleic acid to be delivered, and the like, and can be determined in a routine manner. Exemplary doses for achieving therapeutic effects are titers of at least about $10^5$, $10^6$, $10^7$, $10^8$, $10^9$, $10^{10}$, $10^{11}$, $10^{12}$, $10^{13}$, $10^{14}$, $10^{15}$, $10^{16}$, $10^{17}$, $10^{18}$ transducing units, optionally about $10^8$ to about $10^{15}$ transducing units.

In particular embodiments, more than one administration (e.g., two, three, four or more administrations) may be employed to achieve the desired level of gene expression over a period of various intervals, e.g., daily, weekly, monthly, yearly, etc.

Exemplary modes of administration include systemic administration, e.g., intravenous administration.

Delivery to a target tissue can also be achieved by delivering a depot comprising the virus vector. In representative embodiments, a depot comprising the virus vector is implanted into the tissue or the tissue can be contacted with a film or other matrix comprising the virus vector. Such implantable matrices or substrates are described in U.S. Pat. No. 7,201,898.

In particular embodiments, a virus vector according to the present invention is administered systematically, e.g., intravenously, to treat, delay the onset of and/or prevent symptoms associated with MPS IIIB.

Thus, as one aspect, the invention further encompasses a method of delivering NAGLU to a subject, comprising administering to the subject an effective amount of an AAV particle that expresses NAGLU, thereby delivering NAGLU to the subject.

In another aspect, the invention further encompasses a method of treating, delaying the onset of, and/or preventing MPS IIIB or one or more symptoms associated with MPS IIIB in a subject in need thereof, comprising administering to the subject a therapeutically effective amount of an AAV particle that expresses NAGLU, thereby treating, delaying the onset of, and/or preventing MPS IIIB or one or more symptoms associated with MPS IIIB in the subject.

In the methods of the invention, the subject may be one has been diagnosed with MPS IIIB or is suspected of having MPS IIIB. In certain embodiments, the subject is an infant or child, e.g., less than 18 years old, e.g., less than 18, 17, 16, 15, 14, 13, 12, 11, 10, 9, 8, 7, 6, or 5 years old. In some embodiments, the subject has not developed symptoms of MPS IIIB.

Injectables can be prepared in conventional forms, either as liquid solutions or suspensions, solid forms suitable for solution or suspension in liquid prior to injection, or as emulsions. Alternatively, one may administer the virus vector and/or virus capsids of the invention in a local manner, for example, in a depot or sustained-release formulation. Further, the virus vector and/or virus capsid can be delivered adhered to a surgically implantable matrix (e.g., as described in U.S. Patent Publication No. 2004-0013645).

Having described the present invention, the same will be explained in greater detail in the following examples, which are included herein for illustration purposes only, and which are not intended to be limiting to the invention.

Example 1

Development of Improved rAAV-hNAGLU Vectors rAAV vector product: To develop more effective gene therapy products for treating MPS IIIB, 2 rAAV vector plasmids were constructed to produce second generation rAAV vectors. The single-strand rAAV vector genome contains only minimal elements required for transgene expression, including AAV2 terminal repeats, SV40 splicing signal, codon-optimized hNAGLU cDNA (hNAGLU$^{op}$) and SV40 Poly A signal, controlled by a hybrid CBA promoter with CMV enhancer or a CMV promoter (CMV). FIG. 1 illustrates the structure of rAAV-CBA-hNAGLU$^{op}$ viral vector genome.

Codon-modification enhanced secretion of rNAGLU: To assess the impacts of codon-modification on the transgene product, the rAAV-hNAGLU$^{op}$ constructs were tested in vitro in HEK293 cells and/or Hela cells by transfection, using the first generation rAAV-CMV-hNAGLU vector construct as control. rAAV-CBA-hNAGLU$^{op}$ and rAAV-CMV-hNAGLU$^{op}$ constructs resulted in significant increases of NAGLU activity (per ml) in the media and decreases of NAGLU activity (per mg protein) in cell lysates, compared to rAAV-CMV-hNAGLU (FIGS. 2A-2B). Total combined NAGLU activity levels (cell lysates+media/transfection plate) were significantly higher in samples transfected with rAAV-CBA-hNAGLU$^{op}$ and rAAV-CMV-hNAGLU$^{op}$ than in samples transfected with the control rAAV-CMV-hNAGLU (FIG. 2C). These data indicate that the codon-optimization increased the expression of rNAGLU, and more importantly, with significantly enhanced enzyme secretion of the recombinant enzyme. It is therefore believed that the codon-modified rAAV-hNAGLU$^{op}$ vectors may have added therapeutic benefits for treating MPS IIIB over the first generation product (rAAV-CMV-hNAGLU), by improved by-stander effects of rNAGLU due to the improved rNAGLU expression and enhanced rNAGLU secretion.

Therapeutic impact of systemic rAAV9-hNAGLU$^{op}$ gene delivery for treating MPS IIIB in mice: MPS IIIB mice (NAGLU knockout through disruption of exon 6 of the gene) were treated at age 1 month, 3 months, or 6 months with an IV injection of $1\times10^{13}$ vg/kg, or $2\times10^{13}$ vg/kg rAAV9-CBA-hNAGLU$^{op}$ vector via tail vein. Non-treated MPS IIIB and WT littermates were used as controls. The animals were tested for behavior performance at age 7 months and observed for longevity. Necropsies were performed at 1 week, 1 month, or 7 months post injection (pi), or at the humane endpoint, to assess rNAGLU expression, lysosomal storage pathology, vector biodistribution and histopathology. Table 2 summarizes the study design.

TABLE 2

| | | | | | | | | | |
|---|---|---|---|---|---|---|---|---|---|
| Study design: systemic rAAV9-CBA-hNAGLU delivery in MPS IIIB mice | | | | | | | | | |
| | Vector | | | Number of animals (n) | | | | | |
| | dose | Injection | | | | Tissue analyses | | | |
| Cohorts | (vg/kg) | age (m) | Total | Behavior* | 7 d pi | 1 m pi | 7 m pi | End | Longevity |
| 1. MPS | $1 \times 10^{13}$ | 1 | 13 | 12 | — | — | 4 | 2 | 9** |
| 2. MPS | $2 \times 10^{13}$ | 1 | 9 | 3 | — | 4 | — | — | 3** |
| 3. MPS | $2 \times 10^{13}$ | 3 | 6 | — | 2 | 4 | — | — | 0 |
| 4. MPS | $2 \times 10^{13}$ | 6 | 11 | 9 | — | 2 | — | 3 | 9 |
| 5. MPS# | — | — | 33 | 16 | — | 4 | 6 | n/a | 23 |
| 6. WT# | — | — | 41 | 17 | — | 4 | 6 | n/a | 31 |

*Behavior test at 6 m pi;

**ongoing;

combined from multiple historical studies

A similar study was carried out with rAAV9-CMV-hNA-GLU$^{op}$. MPS IIIB mice were treated at age 1 month, 3 months or 6 months with a IV injection of $1 \times 10^{13}$ vg/kg, or $2 \times 10^{13}$ vg/kg rAAV9-rAAV9-CMV-hNAGLU$^{op}$ vector via tail vein. Non-treated MPS IIIB and WT littermates were used as controls. The animals were tested for behavior performance at age 7 months and observed for longevity. Necropsies were performed at 1 wk, 1 month or 7 months post injection (pi), or at the humane endpoint, to assess rNAGLU expression, the correction of lysosomal storage pathology, vector biodistribution and histopathology. Table 3 summarizes the study designs.

TABLE 3

| | Vector | | Number of animals (n) | | | | | | |
|---|---|---|---|---|---|---|---|---|---|
| | dose | Injection | | | Tissue analyses | | | | |
| Cohorts | (vg/kg) | age (m) | Total | Behavior* | 7 d pi | 1 m pi | 7 m pi | End** | Longevity |
| 1. MPS | $1 \times 10^{13}$ | 1 | 12 | 12 | — | — | 4 | 2 | 8 |
| 2. MPS | $2 \times 10^{13}$ | 3 | 10 | — | 2 | 8 | — | — | — |
| 3. MPS | $2 \times 10^{13}$ | 6 | 11 | 9 | — | 2 | — | 2 | 9 |
| 5. MPS# | — | — | 33 | 16 | — | 4 | 6 | n/a | 23 |
| 6. WT# | — | — | 41 | 17 | — | 4 | 6 | n/a | 31 |

Study design: systemic rAAV9-CMV-hNAGLU delivery in MPS IIIB mice

*Behavior test at age 7 m;
**humane endpoint, tissues not available from dead mice;
combined from multiple historical studies Rapid and persistent restoration of functional NAGLU in MPS IIIB mice after an IV injection of rAAV9-CBA-hNAGLU$^{op}$: NAGLU activity was detected at or above normal levels in the majority of tested tissues from all vector-treated MPS IIIB mice, at 1 week (FIG. 3A) and 1 month pi (FIGS. 3A-3C), with the exception of kidney. These data also showed that tissue NAGLU activity persisted to the endpoint (FIGS. 3B-3C), though there were decreases over time. These data demonstrate the rapid and persistent restoration of functional rNAGLU in the CNS and peripheral tissues, supporting long-lived therapeutic potential of rAAV9-CBA-hNAGLU$^{op}$ via a systemic delivery.

Figures 4A, 4B, 4C:
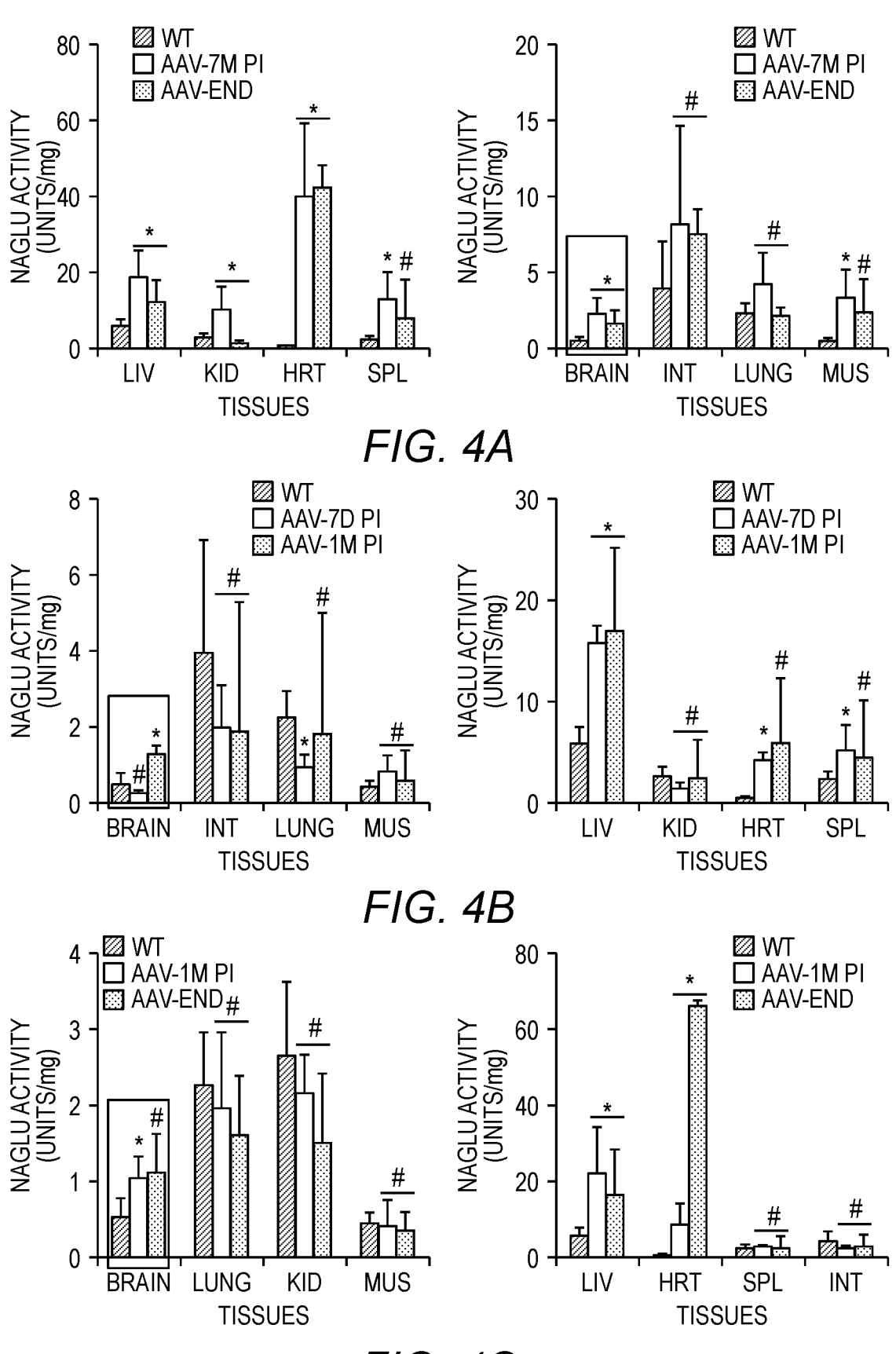
FIGS. 4A-4C show AAV9-mediated persistent restoration of NAGLU activity in the CNS and peripheral tissues in MPS IIIB mice following an IV delivery of rAAV9-CMV-hNAGLU$^{op}$. MPS IIIB mice were treated at age 1 month (A), 3 months (B), or 6 months (C) with a IV injection of $1 \times 10^{13}$ vg/kg (A), or $2 \times 10^{13}$ vg/kg (B, C) rAAV9-CMV-hNAGLU$^{op}$. Tissues were assayed for NAGLU activity at 1 week pi (B), 1 month pi (B, C), 7 m pi (A) or endpoint (A, C). NAGLU activity is expressed as units/mg protein, 1 unit=nmol of 4 MU released/hr. There was no detectable NAGLU activity in tissues in non-treated MPS IIIB mice. m/m: Injection age/testing time. *: p<0.05 vs. WT; #: p>0.05 vs. WT.

Rapid and persistent restoration of functional NAGLU in MPS IIIB mice after an IV injection of rAAV9-CMV-hNAGLU$^{op}$: NAGLU activity was detected at or above normal levels in the majority of tested tissues from all vector-treated MPS IIIB mice, at 1 wk (FIG. 4B) and 1 m pi (FIGS. 4B-4C). The data also showed that tissue NAGLU activity persisted to the endpoint (FIGS. 4A, 4C), though there were decreases over time. These data demonstrate the rapid and persistent restoration of functional rNAGLU in the CNS and peripheral tissues, supporting long-lived therapeutic potential of rAAV9-CMV-hNAGLU$^{op}$ via a systemic delivery.

Figures 5A, 5B, 5C:
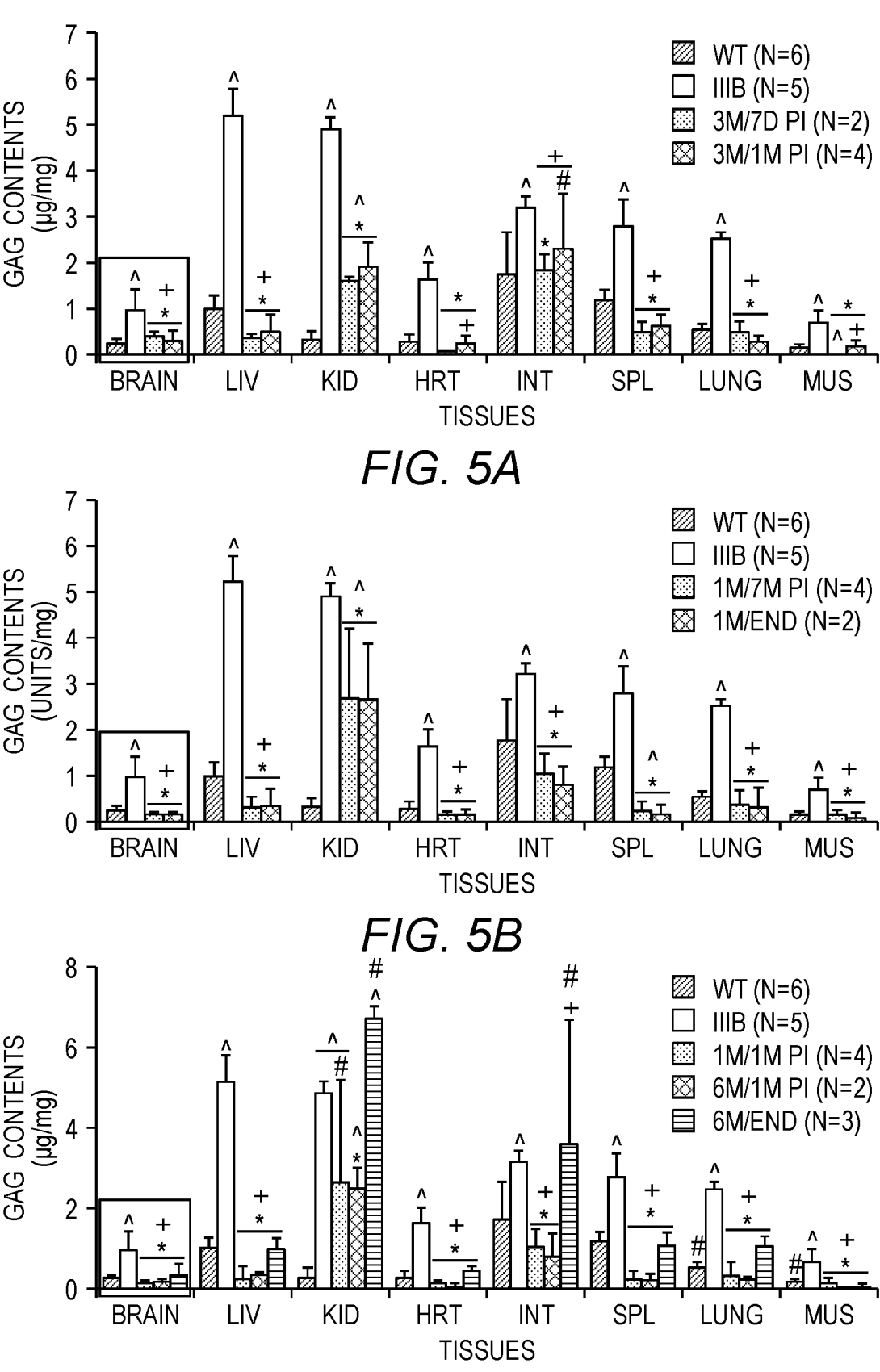
FIGS. 5A-5C show clearance of GAG contents in the CNS and peripheral tissues in MPS IIIB mice following an IV rAAV9 vector delivery. MPS IIIB mice were treated at age 1 month (B, C), 3 months (A) or 6 months (C) with an IV injection of $1 \times 10^{13}$ vg/kg (B) or $2 \times 10^{13}$ vg/kg (A, C) rAAV9-CBA-hNAGLU$^{op}$. Tissues were assayed for GAG contents at 7 days pi (A), 1 month pi (A, C), 7 months pi (B) or endpoint (B, C). GAG contents are expressed as μg/mg wet tissue. WT: wt mice; m/m: Injection age/testing time. *: p<0.05 vs. IIIB; #: p>0.05 vs. IIIB; ^: p<0.05 vs. WT; +: p>0.05.

Clearance of lysosomal GAG storage pathology and astrocytosis: To further assess the functionality of AAV9-mediated rNAGLU, tissues were assayed for GAG content at different time points pi. The results showed that an IV injection of rAAV9-CBA-hNAGLU$^{op}$ vector resulted in significant reduction of GAG content to normal levels in the brain and a majority of tested peripheral tissues, except partial GAG reduction in kidney, in all vector treated MPS IIIB mice (FIGS. 5A-5C). The clearance of tissue GAGs was rapid (FIG. 5A) and persisted to the endpoint (FIGS. 5B-5C).

A similar study was carried out with rAAV9-CMV-hNA-GLU$^{op}$. The results showed that an IV injection of rAAV9-

Figure 6A:
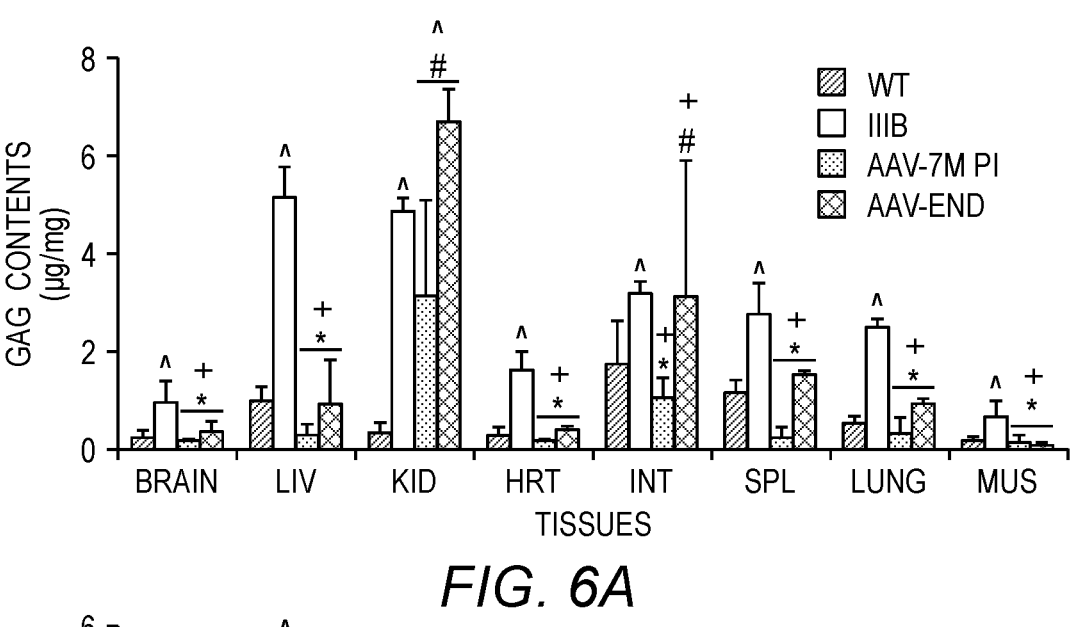
FIGS. 6A-6C show clearance of GAG contents in the CNS and peripheral tissues in MPS IIIB mice following an IV rAAV9-CMV-hNAGLU$^{op}$ delivery. MPS IIIB mice were treated at age 1 month (A), 3 months (B) or 6 months (C) with a IV injection of $1 \times 10^{13}$ vg/kg (A) or $2 \times 10^{13}$ vg/kg (B, C) rAAV9-CMV-hNAGLU$^{op}$. Tissues were assayed for GAG contents at 7 days pi (A), 1 month pi (A, C), 7 months pi (B) or endpoint (B, C). GAG contents is expressed as μg/mg wet tissue. WT: wt mice; m/m: Injection age/testing time. *: p<0.05 vs. IIIB; #: p>0.05 vs. IIIB; ^: p<0.05 vs. WT; +: p>0.05.
Figure 6B:
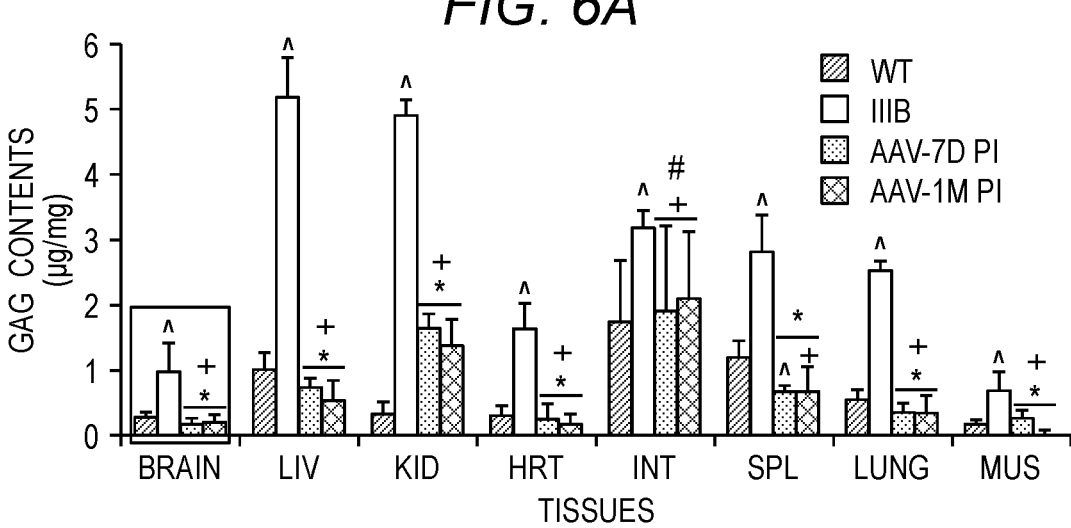
Figure 6C:
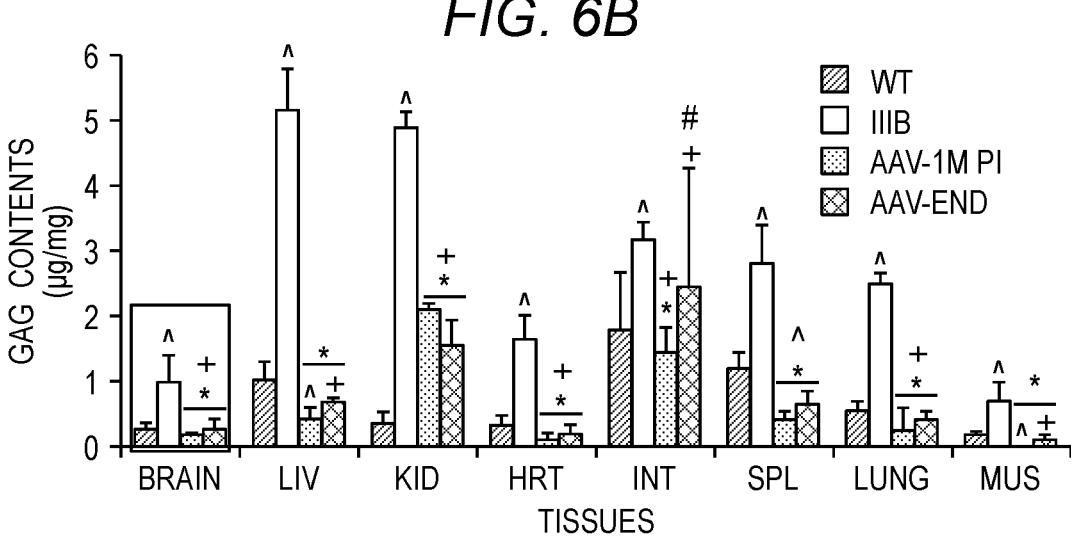

CMV-hNAGLU$^{op}$ vector resulted in significant reduction of GAG content to normal levels in the brain and a majority of tested peripheral tissues, except partial GAG reduction in kidney, in all vector treated MPS IIIB mice (FIGS. 6A-6C). The clearance of tissue GAGs was rapid (FIG. 6B) and persisted to the endpoint (FIGS. 6A, 6C).

Figure 7A:
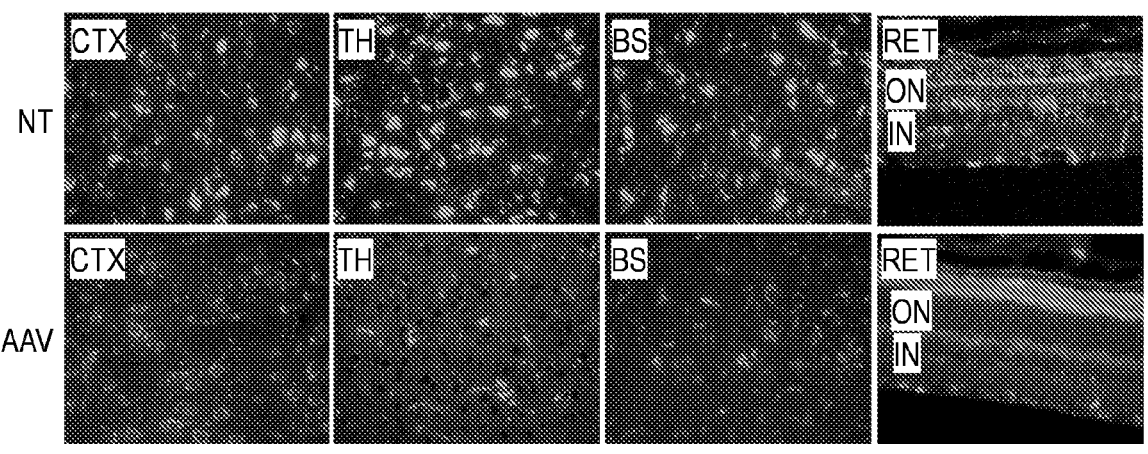
FIGS. 7A-7C show correction of lysosomal storage pathology and astrocytosis. MPS IIIB mice were treated with an IV injection of $1 \times 10^{13}$ vg/kg rAAV9-CBA-hNA-GLU$^{op}$ at age 1 month and necropsy was performed at 7 months pi for tissue analyses. Paraffin tissue sections (4 μm) were assayed by immunofluorescence for lysosomal associated membrane protein 1 (LAMP1, Red fluorescence) (A, C) or GFAP (green fluorescence) (B). A & B: brain and eye tissues: CTX: cerebral cortex; TH: thalamus; BS: brain stem; Ret: retina; ON: outer nuclear layer; IN: inner nuclear layer. C. somatic and eye tissues: Liv: liver; Lung; Spl: spleen; Cil: ciliary body of eye; NT: non-treated MPS IIIA; AAV9: vector treated MPS IIIB mice.
Figure 7B:
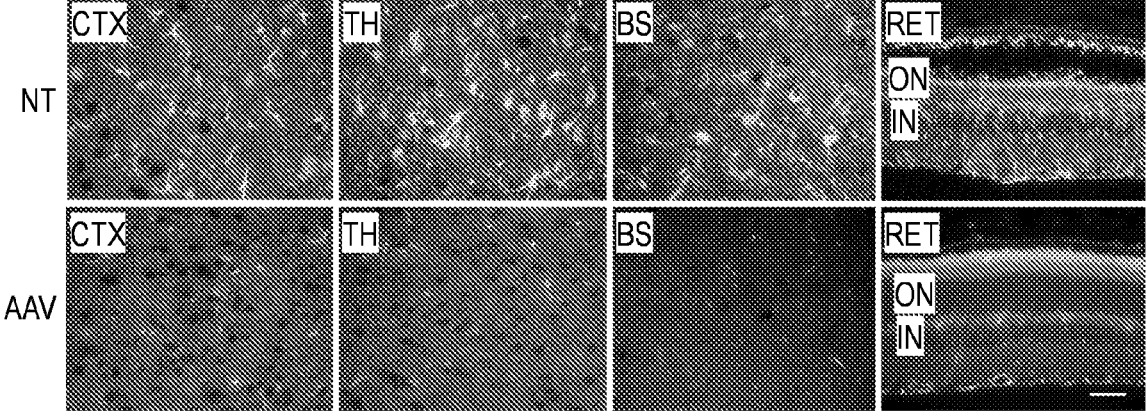
Figure 7C:
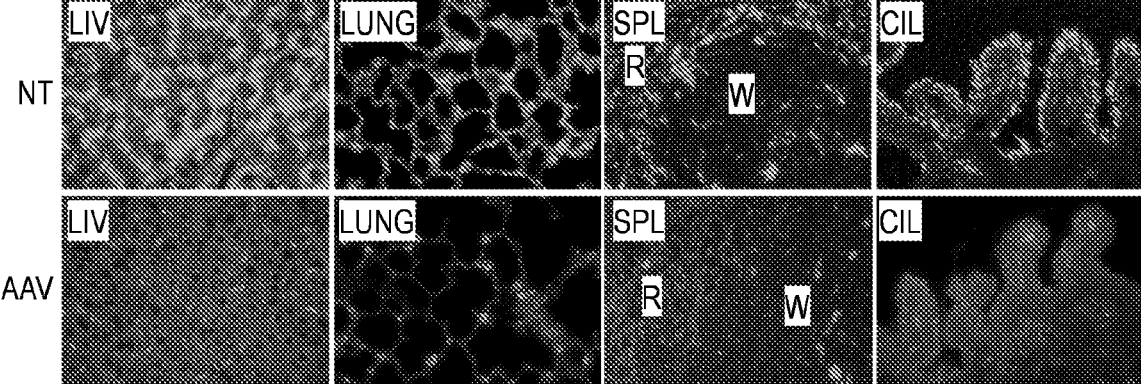

Immunofluorescence (IF) staining showed clearance of the LAMP1 lysosomal marker throughout brain and eye (FIG. 7A) and the majority of the tested somatic tissues (FIG. 7C). These data support that the rAAV9-mediated rNAGLU is functional, leading to rapid and complete clearance of GAG storage in the CNS and the peripheral tissues.

IF staining also showed the clearance of GFAP-positive signals in the brain and retina (FIG. 7B), indicating amelioration of astrocytosis and neuroinflammation in the CNS and optical nervous system.

Figures 8A, 8B:
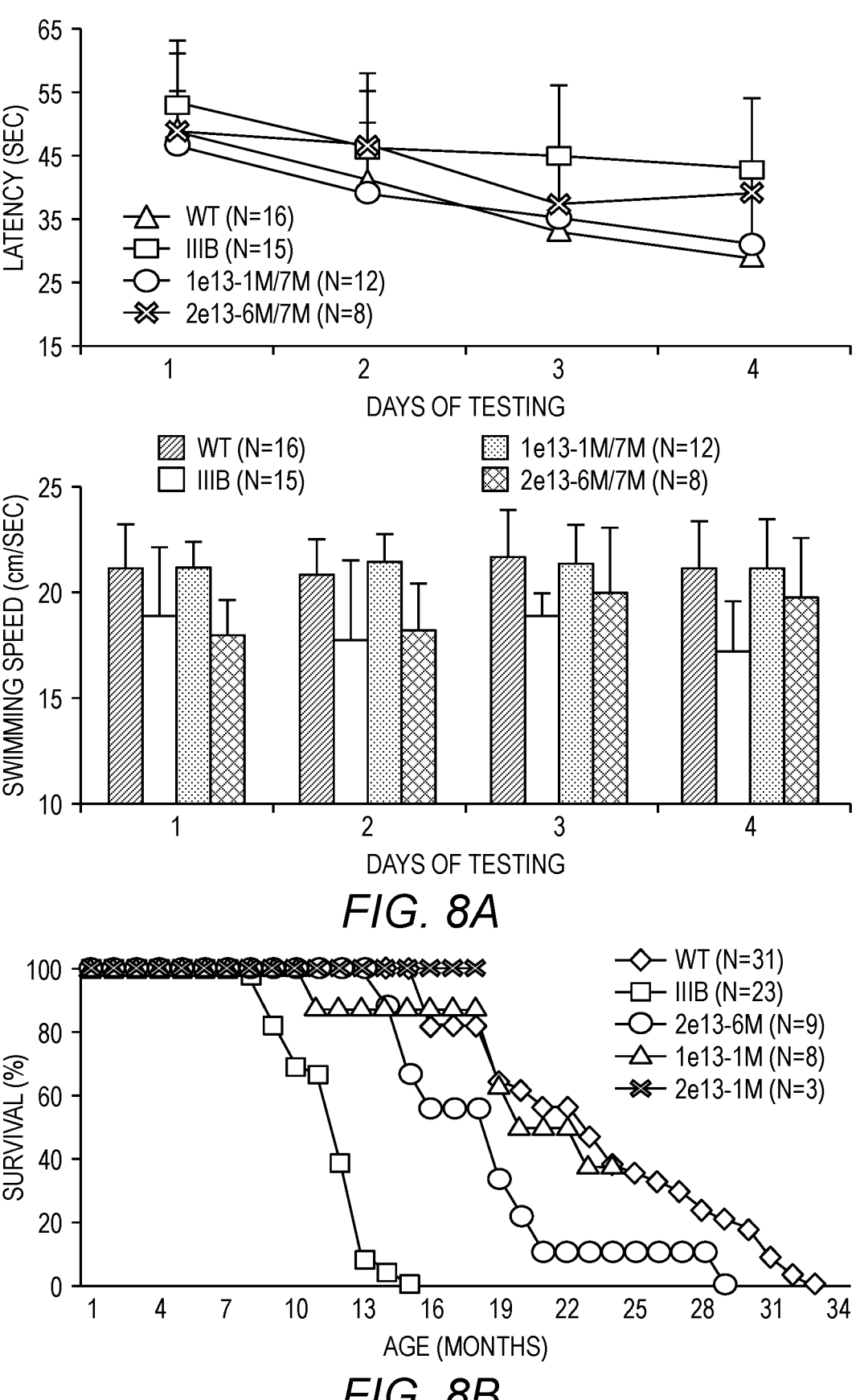
FIGS. 8A-8B show correction of behavior deficits and extension of survival in MPS IIIB mice following a systemic delivery of rAAV9-CBA-hNAGLU$^{op}$. MPS IIIB mice were treated with an IV injection of $1 \times 10^{13}$ vg/kg, or $2 \times 10^{13}$ vg/kg scAAV9-CBA-hNAGLU$^{op}$ vector at age 1 month or 6 months, and were tested for behavior in a hidden task and swimming ability in Morris water maze test at age 7 months (A). WT and non-treated MPS IIIB mice were used as controls. m/m: injection age/testing age. Subsets of animals were observed for longevity (B).

Functional benefits: correction of behavior deficits and extension of survival: To assess the functional benefits of systemic rAAV9-CBA-hNAGLU$^{op}$ gene delivery, the animals were tested at age 7 months for cognitive behavior in the Morris water maze test. MPS IIIB mice treated at age 1 month with $1 \times 10^{13}$ vg/kg vector were tested at age 7 months, and showed normalized latency to find the hidden platform and swimming speed (FIG. 8A), indicating the correction of cognitive and motor function. MPS IIIB mice treated at age 6 months with $2 \times 10^{13}$ vg/kg vector showed partial correction in latency to find the hidden platform and swimming ability, when tested at age 7 months (FIG. 8A). Notably, these animals were treated at advanced disease stage, and likely need a longer time for the correction of the neuropathological damages, given that it was only 1 month pi when tested, as observed in previous studies in MPS IIIA mice (Fu et al., Mol. Ther. Meth. Clin. Dev. 3:16036, doi:10.1038/mtm.2016.36 (2016)).

Longevity studies showed significantly extended survival in MPS IIIB mice treated at age 1 month with $1 \times 10^{13}$ vg/kg rAAV9-CBA-hNAGLU$^{op}$, and at age 1 month or 6 months with $2 \times 10^{13}$ vg/kg rAAV9-CBA-hNAGLU$^{op}$ (FIG. 8B). Importantly, while early vector treatment showed near normalized survival in MPS IIIB mice, the majority of rAAV9-treated animals lived within a normal range of lifespan (FIG. 8B). These data support the correction and reversal of neurological disorders, since premature death is attributed to severe neurological manifestations.

A similar study was carried out with rAAV9-CMV-hNA-GLU$^{op}$. MPS IIIB mice treated at age 6 m with $2 \times 10^{13}$ vg/kg vector were tested at age 8 months, and showed near normalized latency to find the hidden platform and swimming speed (FIG. 9A), indicating the correction of cognitive and motor function. Notably, these animals were treated at advanced disease stage, and were only 2 months pi when tested. Therefore, further behavioral improvements are likely as it may need a longer time for the correction of the severe neuropathological damages, as observed in previous studies in MPS IIIA mice (Fu et al., Mol. Ther. Meth. Clin. Dev. 3:16036, doi:10.1038/mtm.2016.36 (2016)).

Figures 9A, 9B:
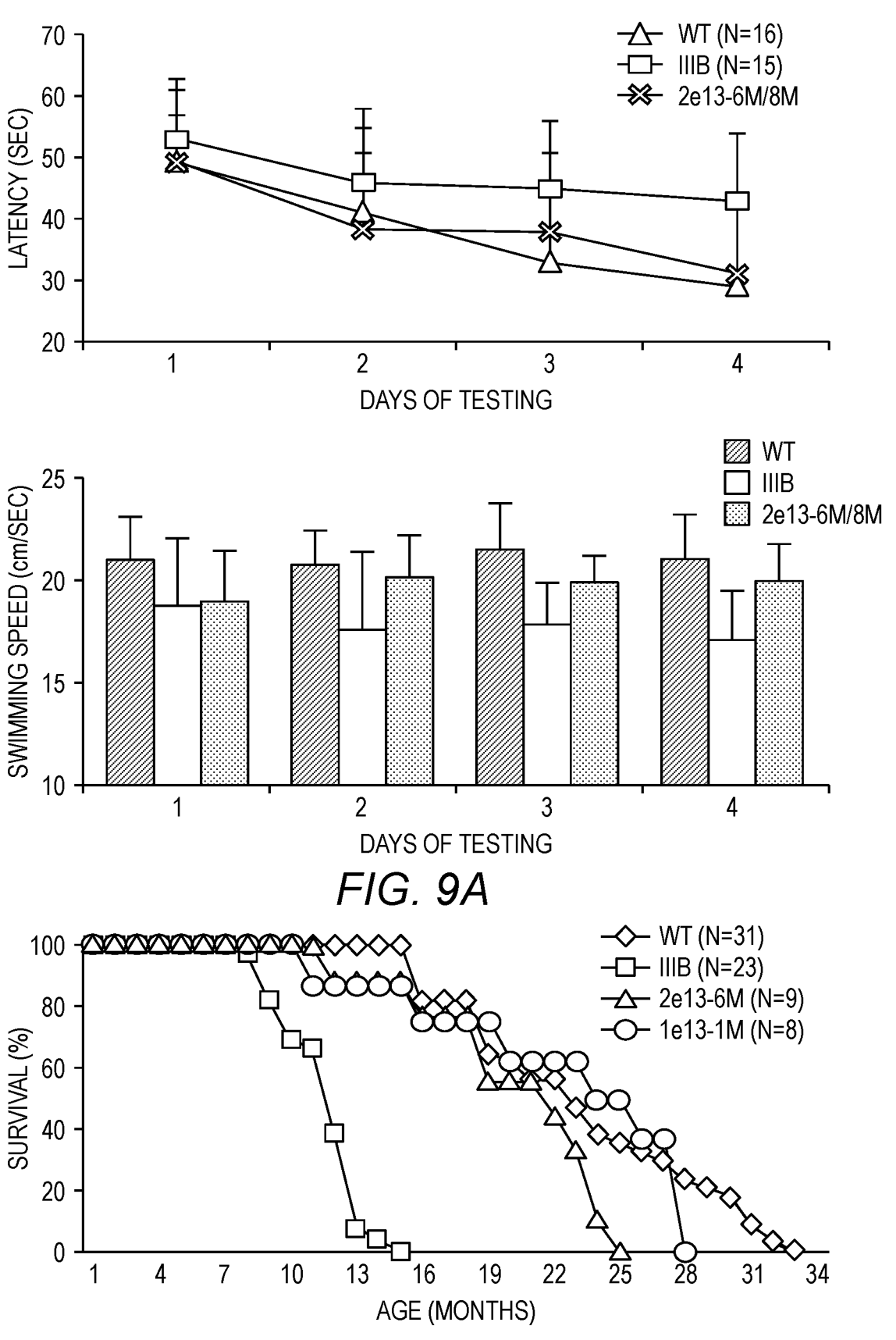
FIGS. 9A-9B show correction of behavior deficits and extension of survival in MPS IIIB mice following a systemic delivery of rAAV9-CMV-hNAGLUop. MPS IIIB mice were treated with an IV injection of $1 \times 10^{13}$ vg/kg, or $2 \times 10^{13}$ vg/kg scAAV9-CBA-hNAGLUop vector at age 1 month or 6 months, and were tested for behavior in a hidden task and swimming ability in Morris water maze at age 8 months (A). Subsets of animals were observed for longevity (B). WT and non-treated MPS IIIB mice were used as controls. m/m: injection age/testing age.

Longevity studies showed significantly extended survival in MPS IIIB mice treated at age 1 month with 1×10$^{13}$ vg/kg rAAV9-CMV-hNAGLU$^{op}$, and at age 1 month or 6 months with 2×10$^{13}$ vg/kg rAAV9-CMV-hNAGLU$^{op}$ (FIG. 9B). Importantly, while early vector treatment showed near normalized survival in MPS IIIB mice, the majority of rAAV9-treated animals lived within a normal range of lifespan (FIG. 9B). These data support the correction and reversal of neurological disorders, as premature death is attributed to severe neurological manifestations.

Figure 10A:
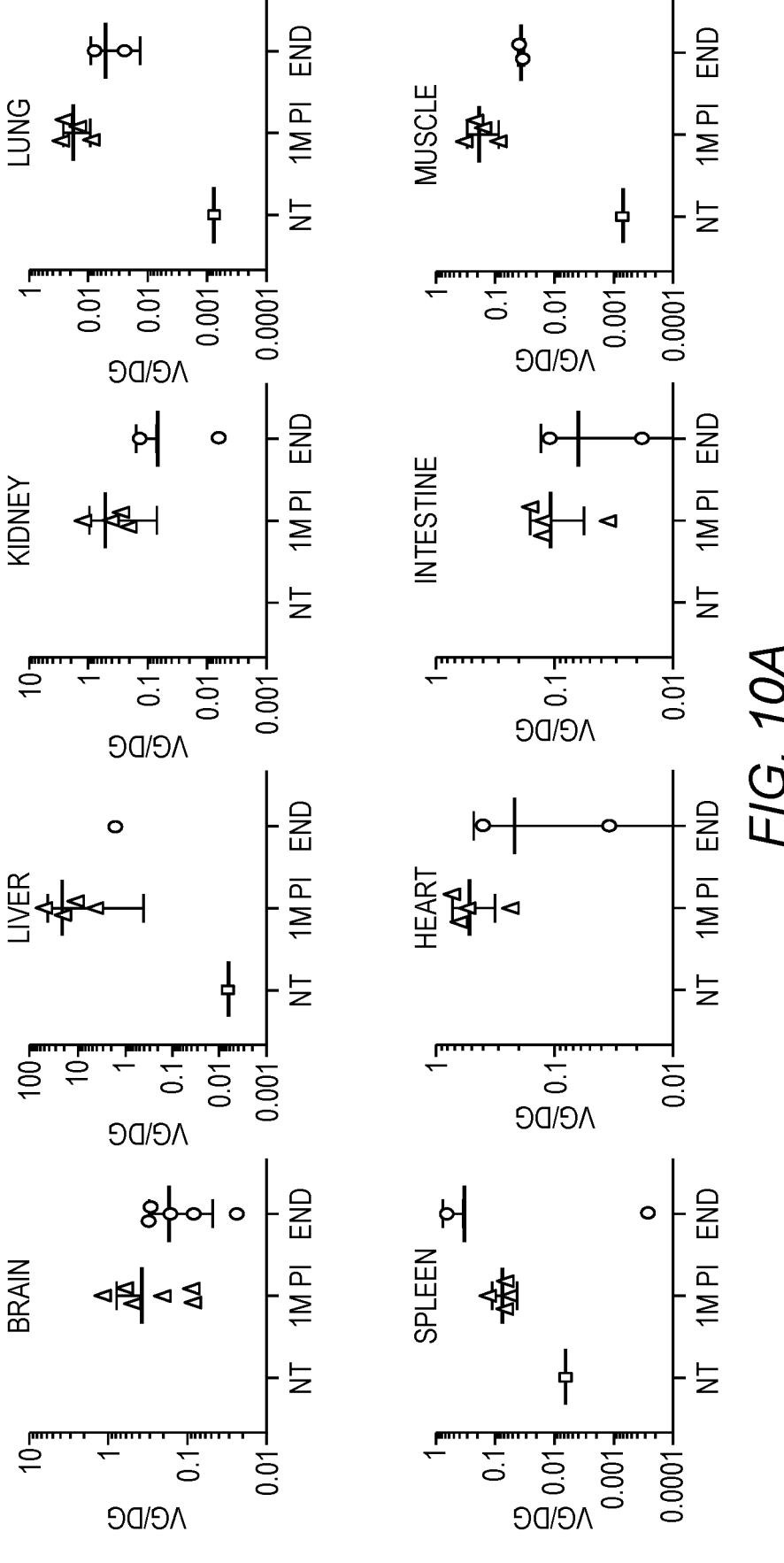
FIGS. 10A-10B show bio-distribution of systemically delivered rAAV9-CBA-hNAGLU$^{op}$. MPS IIIAB mice were treated by an IV injection of $1 \times 10^{13}$ vg/kg (A) or $2 \times 10^{13}$ vg/kg (B) rAAV9-CBA-hNAGLU$^{op}$ at age 1 month (A, B), 3 months (B), or 6 months (B). Tissues were assayed by qPCR at different time points pi. Data expressed as vector genome per diploid genome (vg/dg). <0.01 vg/dg was detected in tissue in non-treated mice. NT: non-treated mice; m/m: injection age/testing time.
Figure 10B:
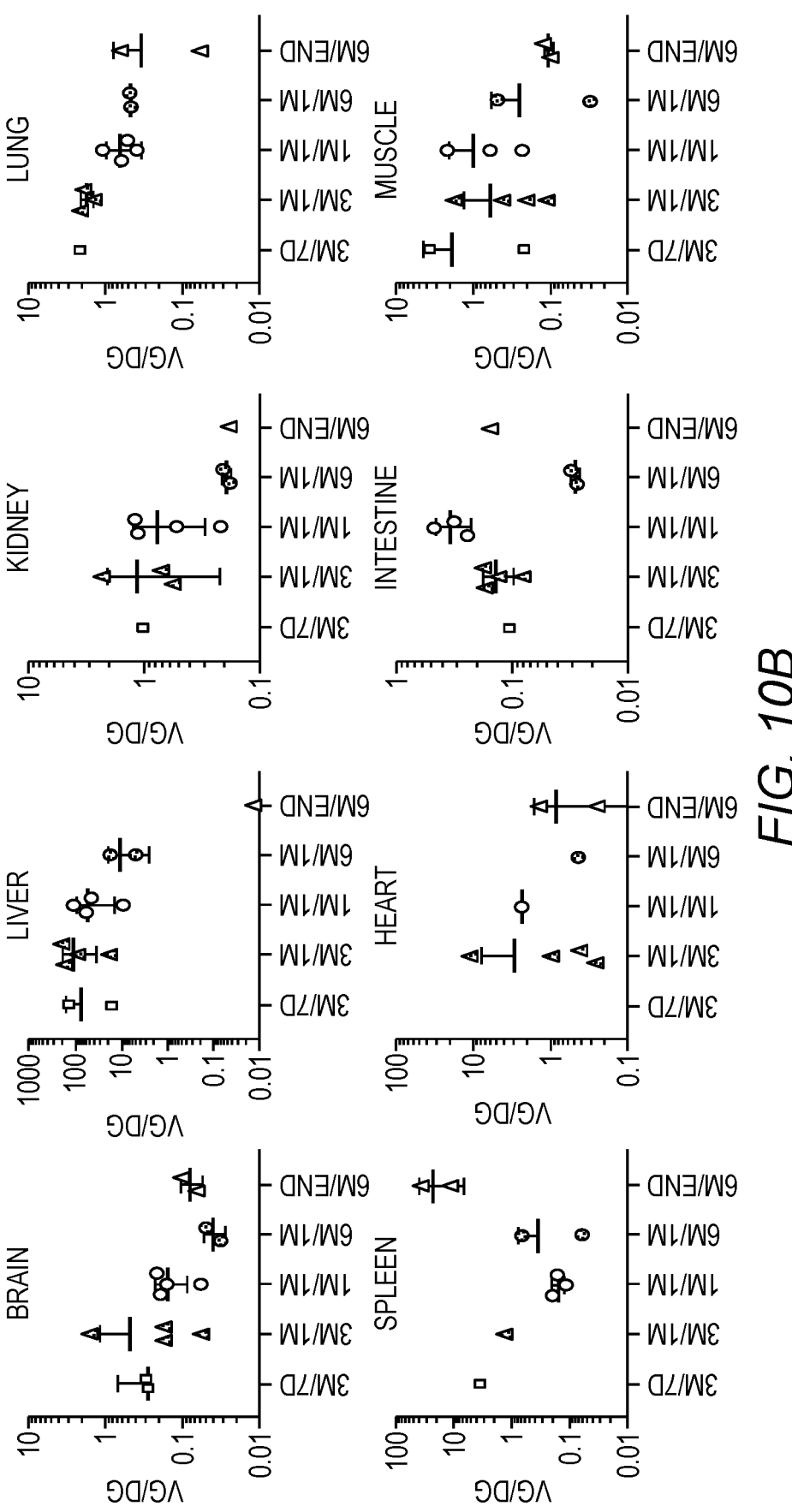

Differential bio-distribution of systemically delivered rAAV9-CBA-hNAGLU$^{op}$ in MPS IIIB mice: qPCR was performed to assay available tissues for rAAV9-CBA-hNA-GLU$^{op}$ vector genome, to assess the bio-distribution of the IV-delivered vector in the CNS and periphery. The result showed differential and persistent bio-distribution of the vector in tissues, with dose-response (FIGS. 10A-10B), correlating to tissue rNAGLU activity levels (FIGS. 3A-3C). A decrease was also observed in vg in tissues over time, especially in liver, possibly due to tissue turnover and the predominantly episomal status of rAAV vector genome.

Summary: The rAAV9-CMV-hNAGLU$^{op}$ was tested by treatment of MPS IIIB mice at different ages via systemic delivery. The data demonstrate that a single IV injection of rAAV9-CBA-hNAGLU$^{op}$ or rAAV9-CMV-hNAGLU$^{op}$ vector is functionally beneficial, leading to the correction and reversal of the disease. Therefore, the rAAV9-CMV-hNA-GLU$^{op}$, or previously tested rAAV9-CBA-hNAGLU$^{op}$ will be further developed towards clinical application.

The rAAV9-hNAGLU$^{op}$ gene therapy product addresses the urgent unmet medical needs for MPS IIIB treatment and offers great potential of significantly improving the quality of life of not only MPS IIIB patients but also their families.

The foregoing is illustrative of the present invention, and is not to be construed as limiting thereof. The invention is defined by the following claims, with equivalents of the claims to be included therein.

That which is claimed is:

1. A recombinant nucleic acid comprising a nucleotide sequence encoding human α-N-acetylglucosaminidase (NAGLU) that is codon-optimized for expression in human cells, wherein the recombinant nucleic acid comprises the nucleotide sequence of SEQ ID NO: 1.

2. A vector comprising the recombinant nucleic acid of claim 1.

3. The vector of claim 2, comprising the sequence of SEQ ID NO:3 or SEQ ID NO:4 or a sequence at least 90% identical thereto.

4. An adeno-associated virus (AAV) vector genome comprising the recombinant nucleic acid of claim 1.

5. The AAV vector genome of claim 4, wherein the AAV vector genome is a self-complementary AAV vector genome.

6. The AAV vector genome of claim 4, wherein the recombinant nucleic acid is operably linked to a constitutive promoter.

7. The AAV vector genome of claim 6, wherein the constitutive promoter is the CBA promoter.

8. The AAV vector genome of claim 6, wherein the constitutive promoter is the CMV promoter.

9. A cell in vitro comprising the AAV vector genome of claim 4.

10. An AAV particle comprising the AAV vector genome of claim 4.

11. A method of producing a recombinant AAV particle comprising an AAV capsid, the method comprising:

providing a cell in vitro with AAV Cap and AAV Rep coding sequences, the AAV vector genome of claim 4, and helper functions for generating a productive AAV infection; and allowing assembly of the recombinant AAV particle comprising the AAV capsid and encapsidating the AAV vector genome.

12. An AAV particle produced by the method of claim 11.

13. The AAV particle of claim 10, wherein the AAV particle is an AAV9 particle.

14. A pharmaceutical formulation comprising the AAV particle of claim 10 and a pharmaceutically acceptable carrier.

15. A method of expressing NAGLU in a cell, comprising contacting the cell with an effective amount of the AAV particle of claim 10, thereby expressing NAGLU in the cell.

16. A method of increasing secretion of NAGLU from a cell, comprising contacting the cell with an effective amount of the AAV particle of claim 10, thereby increasing secretion of NAGLU from the cell relative to the secretion of NAGLU after contacting the cell with an AAV particle comprising a nucleic acid comprising the wild-type sequence for NAGLU.

17. A method of delivering NAGLU to a subject, comprising administering to the subject an effective amount of the pharmaceutical formulation of claim 14, thereby delivering NAGLU to the subject.

18. A method of treating or delaying the onset of mucopolysaccharidosis IIIB (MPS IIIB) in a subject in need thereof, comprising administering to the subject a therapeutically effective amount of the pharmaceutical formulation of claim 14, thereby treating or delaying the onset of MPS IIIB in the subject.

19. The method of claim 18, wherein the AAV particle is administered to the subject systemically.

\* \* \* \* \*